(12) United States Patent
Cole et al.

(10) Patent No.: US 7,913,892 B2
(45) Date of Patent: Mar. 29, 2011

(54) ENDOSCOPIC STAPLING DEVICES AND METHODS

(75) Inventors: David Cole, San Mateo, CA (US); Andrew Smith, San Francisco, CA (US)

(73) Assignee: Barosense, Inc., Durham, NC (US)

( * ) Notice: Subject to any disclaimer, the term of this patent is extended or adjusted under 35 U.S.C. 154(b) by 279 days.

(21) Appl. No.: 12/053,182

(22) Filed: Mar. 21, 2008

(65) Prior Publication Data

US 2009/0236391 A1    Sep. 24, 2009

Related U.S. Application Data

(62) Division of application No. 12/050,169, filed on Mar. 18, 2008.

(51) Int. Cl.
*A61B 17/068* (2006.01)

(52) U.S. Cl. .............. 227/176.1; 227/19; 227/180.1; 606/139; 606/219

(58) Field of Classification Search ............ 227/19, 227/176.1, 175.1, 178.1, 180.1; 606/139, 606/151, 153, 219
See application file for complete search history.

(56) References Cited

U.S. PATENT DOCUMENTS

| | | | |
|---|---|---|---|
| 1,408,865 A | 3/1922 | Cowell |
| 3,663,965 A | 5/1972 | Lee et al. |
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |

(Continued)

FOREIGN PATENT DOCUMENTS

CH    680263 A5    7/1992

(Continued)

OTHER PUBLICATIONS

U.S. Appl. No. 12/050,169, Cole et al.

(Continued)

*Primary Examiner* — Scott A Smith
(74) *Attorney, Agent, or Firm* — King & Spalding LLP; Peter J. Dehlinger; Kathleen A. Frost

(57) ABSTRACT

Described herein are endoscopic staplers used to apply one or more fasteners to body tissue. In one embodiment, a fastener-applying device, which is preferably a stapler, is passed transorally into the stomach and used to plicate stomach tissue by engaging tissue from inside of the stomach and drawing it inwardly. In the disclosed embodiments, the tissue is drawn inwardly into a vacuum chamber, causing sections of serosal tissue on the exterior of the stomach to be positioned facing one another. The disclosed staplers allow the opposed sections of tissue to be moved into contact with one another, and preferably deliver staples for maintaining contact between the tissue sections at least until serosal bonds form between them. Each of these steps may be performed wholly from the inside of the stomach and thus can eliminate the need for any surgical or laparoscopic intervention. After one or more plications are formed, medical devices may optionally be coupled to the plication(s) for retention within the stomach.

28 Claims, 22 Drawing Sheets

U.S. PATENT DOCUMENTS

| | | | |
|---|---|---|---|
| 4,485,805 A | 12/1984 | Foster, Jr. | |
| 4,501,264 A | 2/1985 | Rockey | |
| 4,607,618 A | 8/1986 | Angelchik | |
| 4,641,653 A | 2/1987 | Rockey | |
| 4,648,383 A | 3/1987 | Angelchik | |
| 4,694,827 A | 9/1987 | Weiner et al. | |
| 4,723,547 A | 2/1988 | Kullas et al. | |
| 4,747,849 A | 5/1988 | Galtier | |
| 4,846,836 A | 7/1989 | Reich | |
| 4,848,367 A | 7/1989 | Avant et al. | |
| 4,899,747 A | 2/1990 | Garren et al. | |
| 4,925,446 A | 5/1990 | Garay et al. | |
| 4,946,440 A | 8/1990 | Hall | |
| 4,969,896 A | 11/1990 | Shors | |
| 4,997,084 A | 3/1991 | Opie et al. | |
| 5,006,106 A | 4/1991 | Angelchik | |
| 5,037,021 A | 8/1991 | Mills et al. | |
| 5,061,275 A | 10/1991 | Wallsten et al. | |
| 5,084,061 A | 1/1992 | Gau et al. | |
| 5,088,979 A | 2/1992 | Filipi et al. | |
| 5,163,952 A | 11/1992 | Froix | |
| 5,211,658 A | 5/1993 | Clouse | |
| 5,234,454 A | 8/1993 | Bangs | |
| 5,246,456 A | 9/1993 | Wilkinson | |
| 5,259,399 A | 11/1993 | Brown | |
| 5,263,629 A | 11/1993 | Trumbull et al. | |
| 5,290,217 A | 3/1994 | Campos | |
| 5,306,300 A | 4/1994 | Berry | |
| 5,314,473 A | 5/1994 | Godin | |
| 5,327,914 A | 7/1994 | Shlain | |
| 5,345,949 A | 9/1994 | Shain | |
| 5,355,897 A | 10/1994 | Pietrafitta et al. | |
| 5,401,241 A | 3/1995 | Delany | |
| 5,403,326 A | 4/1995 | Harrison et al. | |
| 5,405,377 A | 4/1995 | Cragg | |
| 5,431,673 A | 7/1995 | Summers et al. | |
| 5,486,187 A | 1/1996 | Schneck | |
| 5,514,176 A | 5/1996 | Bosley, Jr. | |
| 5,535,935 A | 7/1996 | Vidal et al. | |
| 5,542,949 A | 8/1996 | Yoon | |
| 5,562,239 A | 10/1996 | Boiarski et al. | |
| 5,571,116 A | 11/1996 | Bolanos et al. | |
| 5,577,654 A | 11/1996 | Bishop | |
| 5,593,434 A | 1/1997 | Williams | |
| 5,597,107 A | 1/1997 | Knodel et al. | |
| 5,609,624 A | 3/1997 | Kalis | |
| 5,628,786 A | 5/1997 | Banas et al. | |
| 5,630,539 A | 5/1997 | Plyley et al. | |
| 5,647,526 A | 7/1997 | Green et al. | |
| 5,653,743 A | 8/1997 | Martin | |
| 5,662,713 A | 9/1997 | Andersen et al. | |
| 5,673,841 A | 10/1997 | Schulze et al. | |
| 5,674,241 A | 10/1997 | Bley et al. | |
| 5,706,998 A | 1/1998 | Plyley et al. | |
| 5,709,657 A | 1/1998 | Zimmon | |
| 5,720,776 A | 2/1998 | Chuter et al. | |
| 5,749,918 A | 5/1998 | Hogendijk et al. | |
| 5,762,255 A | 6/1998 | Chrisman et al. | |
| 5,771,903 A | 6/1998 | Jakobsson | |
| 5,785,684 A | 7/1998 | Zimmon | |
| 5,820,584 A | 10/1998 | Crabb | |
| 5,839,639 A | 11/1998 | Sauer et al. | |
| 5,848,964 A | 12/1998 | Samuels | |
| 5,855,311 A | 1/1999 | Hamblin et al. | |
| 5,855,601 A | 1/1999 | Bessler et al. | |
| 5,856,445 A | 1/1999 | Korsmeyer | |
| 5,861,036 A | 1/1999 | Godin | |
| 5,868,141 A | 2/1999 | Ellias | |
| 5,887,594 A | 3/1999 | LoCicero, III | |
| 5,897,562 A | 4/1999 | Bolanos et al. | |
| 5,910,144 A | 6/1999 | Hayashi | |
| 5,922,019 A | 7/1999 | Hankh et al. | |
| 5,947,983 A | 9/1999 | Solar et al. | |
| 5,993,473 A | 11/1999 | Chan et al. | |
| 5,993,483 A | 11/1999 | Gianotti | |
| 6,016,848 A | 1/2000 | Egres, Jr. | |
| 6,051,015 A | 4/2000 | Maahs | |
| 6,086,600 A | 7/2000 | Kortenback | |
| 6,098,629 A | 8/2000 | Johnson et al. | |
| 6,102,922 A | 8/2000 | Jakobsson et al. | |
| 6,113,609 A | 9/2000 | Adams | |
| 6,120,534 A | 9/2000 | Ruiz | |
| 6,146,416 A | 11/2000 | Andersen et al. | |
| 6,159,146 A | 12/2000 | El Gazayerli | |
| 6,159,238 A | 12/2000 | Killion et al. | |
| 6,197,022 B1 | 3/2001 | Baker | |
| 6,206,930 B1 | 3/2001 | Burg et al. | |
| 6,245,088 B1 | 6/2001 | Lowery | |
| 6,251,132 B1 | 6/2001 | Ravenscroft et al. | |
| 6,254,642 B1 | 7/2001 | Taylor | |
| 6,258,120 B1 | 7/2001 | McKenzie et al. | |
| 6,264,700 B1 | 7/2001 | Kilcoyne et al. | |
| 6,287,334 B1 | 9/2001 | Moll et al. | |
| 6,302,917 B1 | 10/2001 | Dua et al. | |
| 6,358,197 B1 | 3/2002 | Silverman | |
| 6,416,522 B1 | 7/2002 | Strecker | |
| 6,425,916 B1 | 7/2002 | Garrison et al. | |
| 6,454,785 B2 | 9/2002 | De Hoyos Garza | |
| 6,460,543 B1 | 10/2002 | Forsell | |
| 6,461,366 B1 | 10/2002 | Seguin | |
| 6,494,888 B1 | 12/2002 | Laufer et al. | |
| 6,494,895 B2 | 12/2002 | Addis | |
| 6,503,264 B1 | 1/2003 | Birk | |
| 6,506,196 B1 | 1/2003 | Laufer et al. | |
| 6,527,784 B2 | 3/2003 | Adams et al. | |
| 6,540,789 B1 | 4/2003 | Silverman et al. | |
| 6,544,291 B2 | 4/2003 | Taylor | |
| 6,547,801 B1 | 4/2003 | Dargent et al. | |
| 6,558,400 B2 | 5/2003 | Deem et al. | |
| 6,558,429 B2 | 5/2003 | Taylor et al. | |
| 6,572,627 B2 | 6/2003 | Gabbay | |
| 6,572,629 B2 | 6/2003 | Kalloo | |
| 6,575,896 B2 | 6/2003 | Silverman | |
| 6,592,596 B1 | 7/2003 | Geitz | |
| 6,596,023 B1 | 7/2003 | Nunez et al. | |
| 6,607,555 B2 | 8/2003 | Patterson et al. | |
| 6,627,206 B2 | 9/2003 | Lloyd | |
| 6,632,227 B2 | 10/2003 | Adams | |
| 6,663,639 B1 | 12/2003 | Laufer et al. | |
| 6,675,809 B2 | 1/2004 | Stack et al. | |
| 6,740,098 B2 | 5/2004 | Abrams et al. | |
| 6,740,121 B2 | 5/2004 | Geitz | |
| 6,746,460 B2 | 6/2004 | Gannoe et al. | |
| 6,755,869 B2 | 6/2004 | Geitz | |
| 6,764,518 B2 | 7/2004 | Godin | |
| 6,773,440 B2 | 8/2004 | Gannoe et al. | |
| 6,773,441 B1 | 8/2004 | Laufer et al. | |
| 6,790,214 B2 | 9/2004 | Kraemer et al. | |
| 6,790,237 B2 | 9/2004 | Stinson | |
| 6,821,285 B2 | 11/2004 | Laufer et al. | |
| 6,835,200 B2 | 12/2004 | Laufer et al. | |
| 6,845,776 B2 | 1/2005 | Stack et al. | |
| 6,916,332 B2 | 7/2005 | Adams | |
| 6,932,838 B2 | 8/2005 | Schwartz et al. | |
| 6,960,233 B1 | 11/2005 | Berg et al. | |
| 6,966,875 B1 | 11/2005 | Longobardi | |
| 6,981,978 B2 | 1/2006 | Gannoe | |
| 6,981,980 B2 | 1/2006 | Sampson et al. | |
| 6,994,715 B2 | 2/2006 | Gannoe et al. | |
| 7,011,094 B2 | 3/2006 | Rapackie et al. | |
| 7,020,531 B1 | 3/2006 | Colliou et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,056,305 B2 | 6/2006 | Garza | |
| 7,066,945 B2 | 6/2006 | Hashiba et al. | |
| 7,083,629 B2 | 8/2006 | Weller et al. | |
| 7,090,699 B2 | 8/2006 | Geitz | |
| 7,097,650 B2 | 8/2006 | Weller et al. | |
| 7,097,665 B2 | 8/2006 | Stack et al. | |
| 7,111,627 B2 | 9/2006 | Stack et al. | |
| 7,112,186 B2 | 9/2006 | Shah | |
| 7,120,498 B2 | 10/2006 | Imran et al. | |
| 7,121,283 B2 | 10/2006 | Stack et al. | |
| 7,146,984 B2 | 12/2006 | Stack et al. | |
| 7,147,140 B2 | 12/2006 | Wukusick et al. | |

| Patent | Date | Inventor |
|---|---|---|
| 7,152,607 B2 | 12/2006 | Stack et al. |
| 7,160,312 B2 | 1/2007 | Saadat |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,354,454 B2 | 4/2008 | Stack et al. |
| 7,431,725 B2 | 10/2008 | Stack et al. |
| 7,461,767 B2 | 12/2008 | Viola et al. |
| 7,552,853 B2 * | 6/2009 | Mas et al. .................. 227/175.1 |
| 7,575,144 B2 * | 8/2009 | Ortiz et al. .................. 227/175.1 |
| 7,588,174 B2 * | 9/2009 | Holsten et al. ............. 227/176.1 |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 | 6/2002 | Schurr et al. |
| 2002/0099439 A1 | 7/2002 | Schwartz et al. |
| 2002/0183767 A1 | 12/2002 | Adams et al. |
| 2002/0183768 A1 | 12/2002 | Deem et al. |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0120289 A1 | 6/2003 | McGuckin, Jr. et al. |
| 2003/0158569 A1 | 8/2003 | Wazne |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 | 3/2004 | DeVries et al. |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 | 6/2004 | Levine et al. |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. |
| 2005/0096750 A1 | 5/2005 | Kagan et al. |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0216040 A1 | 9/2005 | Gertner et al. |
| 2005/0216042 A1 | 9/2005 | Gertner |
| 2005/0240279 A1 | 10/2005 | Kagan et al. |
| 2005/0247320 A1 | 11/2005 | Stack et al. |
| 2005/0250980 A1 | 11/2005 | Swanstrom et al. |
| 2005/0251158 A1 | 11/2005 | Sadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267405 A1 | 12/2005 | Shah |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0015006 A1 | 1/2006 | Laurence et al. |
| 2006/0020278 A1 | 1/2006 | Burnette et al. |
| 2006/0058829 A1 | 3/2006 | Sampson et al. |
| 2006/0129094 A1 | 6/2006 | Shah |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0294179 A1 | 11/2008 | Balbierz et al. |
| 2009/0024143 A1 | 1/2009 | Crews et al. |
| 2009/0030284 A1 | 1/2009 | Cole et al. |
| 2009/0125040 A1 | 5/2009 | Hambly et al. |

FOREIGN PATENT DOCUMENTS

| | | |
|---|---|---|
| EP | 0 775 471 A1 | 5/1997 |
| EP | 09-168597 | 6/1997 |

| | | |
|---|---|---|
| EP | 1492478 | 1/2005 |
| EP | 1 602 336 A2 | 12/2005 |
| FR | 2768324 A1 | 3/1999 |
| WO | WO 91/01117 A1 | 2/1991 |
| WO | WO 97/47231 A2 | 12/1997 |
| WO | WO 00/12027 A1 | 3/2000 |
| WO | WO 00/32137 A1 | 6/2000 |
| WO | WO 00/78227 A1 | 12/2000 |
| WO | WO 01/41671 | 6/2001 |
| WO | WO 01/45485 A2 | 6/2001 |
| WO | WO 01/49359 A1 | 7/2001 |
| WO | WO 01/66018 A1 | 9/2001 |
| WO | WO 01/85034 A1 | 11/2001 |
| WO | WO 01/89393 A1 | 11/2001 |
| WO | WO 02/060328 A1 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 A2 | 11/2003 |
| WO | WO 03/094785 | 11/2003 |
| WO | WO 03/099137 A2 | 12/2003 |
| WO | WO 2004/019765 | 3/2004 |
| WO | WO 2004/019787 | 3/2004 |
| WO | WO 2004/032760 A2 | 4/2004 |
| WO | WO 2004/037064 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 A1 | 12/2004 |
| WO | WO 2005/037152 A1 | 4/2005 |
| WO | WO 2005/079673 A2 | 9/2005 |
| WO | WO 2005/096991 A1 | 10/2005 |
| WO | WO 2005/105003 | 11/2005 |
| WO | WO 2006/016894 A1 | 2/2006 |
| WO | WO 2006/055365 A2 | 5/2006 |
| WO | WO 2006/127593 | 11/2006 |
| WO | WO 2007/041598 A1 | 4/2007 |
| WO | WO 2008/030403 | 3/2008 |
| WO | WO 2008/033409 | 3/2008 |
| WO | WO 2008/033474 | 3/2008 |
| WO | WO2008/141288 A1 | 11/2008 |

OTHER PUBLICATIONS

The International Search report and Written Opinion for PCT application PCT/US2008/008726, Oct. 16, 2008, 13 pages (2008).
The International Search report and Written Opinion for PCT application PCT/US2007/019833, Dec. 9, 2007, 11 pages (2007).
The International Search report for PCT application PCT/US2008/063440, search report dated Aug. 1, 2008, 11 pages (2007).
The International Search report and Written Opinion for PCT application PCT/US2007/019940, Mar. 20, 2008, 12 pages (2008).
Stecco, K. et al., "Trans-Oral Plication Formation and Gastric Implant Placement in a Canine Model", Stecco Group, San Jose and Barosnese, Inc., Redwood City, California (2004).
Stecco, K. et al., "Safety of A Gastric Restrictive Implant in a Canine Model", Stecco Group, San Jose and Barosnese, Inc., Redwood City, California (2004).
International Search Report from PCT Patent Application No. PCT/US2002/027177 mailed Feb. 14, 2003.
International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search Report from PCT Patent Application No. PCT/US2007/019227 mailed Feb. 20, 2008.
International Search Report from PCT Patent Application No. PCT/US2008/008729 mailed Aug. 18, 2009.
Felsher, et al., "Mucosal apposition in endoscopic suturing", Gastrointestinal Endoscopy, vol. 58, No. 6, pp. 867-870, (2003).

* cited by examiner

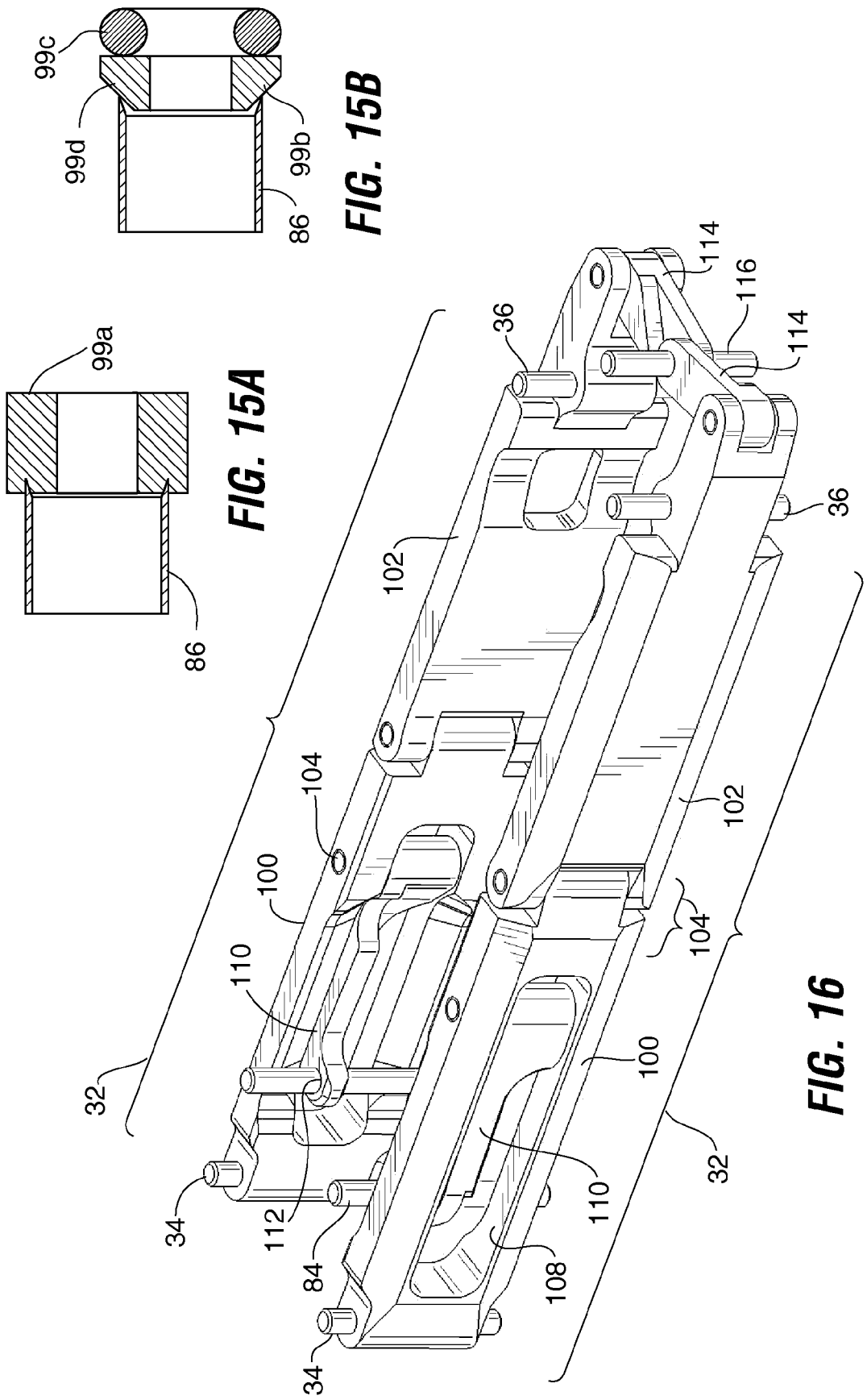

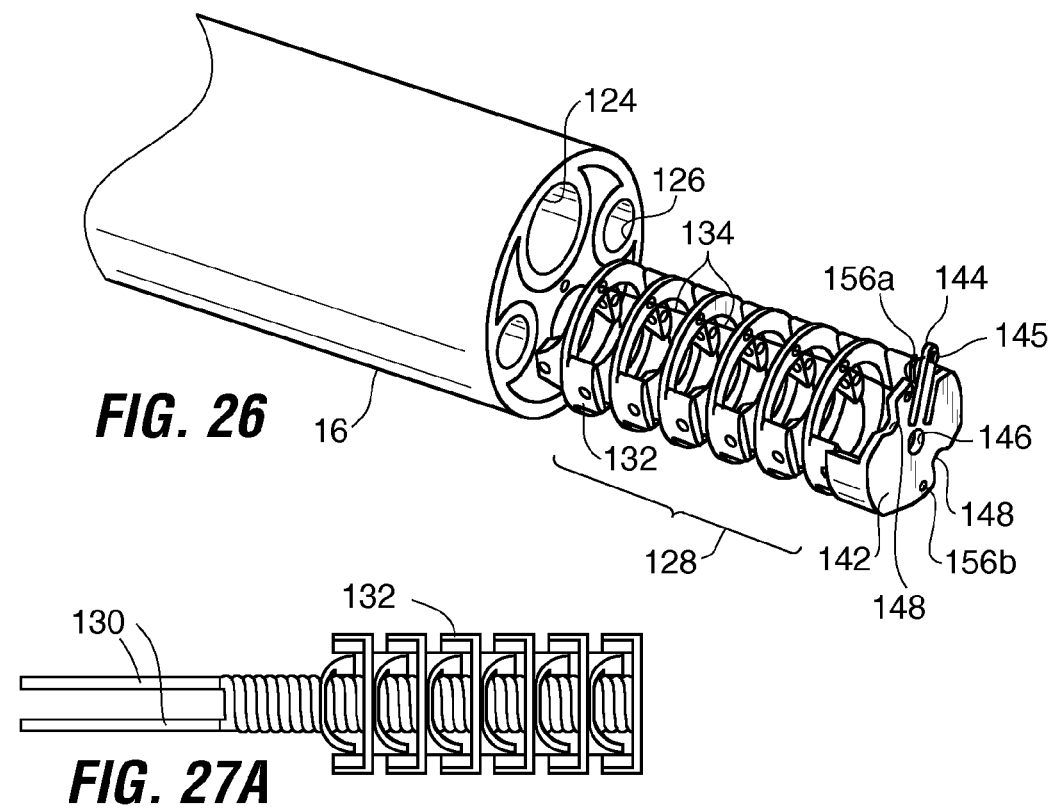
FIG. 26
FIG. 27A
FIG. 27B
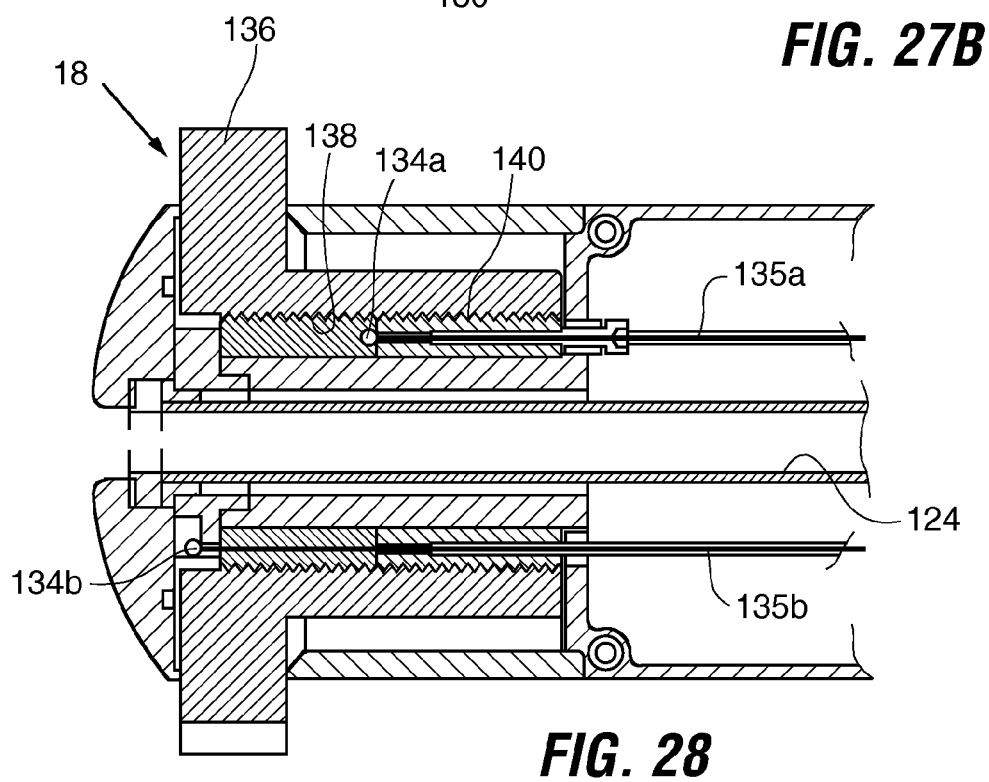
FIG. 28

ENDOSCOPIC STAPLING DEVICES AND METHODS

PRIORITY

This application is a divisional of U.S. patent application Ser. No. 12/050,169, filed Mar. 18, 2008, pending, entitled ENDOSCOPIC STAPLING DEVICES AND METHODS, and is incorporated herein by reference.

FIELD OF THE INVENTION

The present invention relates generally to the field of systems and methods for performing endoscopic surgery, and specifically to systems and methods for endoscopic stapling of tissue within body cavities.

BACKGROUND OF THE INVENTION

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

There are a number of applications for endoscopic application of fasteners such as staples to tissue within a body cavity. Some of those applications involve forming tissue structures such as plications or folds in tissue of the body cavity.

Several prior applications, including International Application No. WO 2005/037152 having an international filing date of Oct. 8, 2004 and U.S. application Ser. No. 11/439,461, filed May 23, 2006 (both incorporated herein by reference) describe methods according to which medical implants are coupled to tissue structures formed within the stomach. According to these applications, devices for inducing weight loss (e.g. by restricting and/or obstructing flow of food into the stomach, and/or by occupying a portion of the stomach volume) may be coupled to tissue tunnels or plications formed from stomach tissue.

For example, U.S. application Ser. No. 11/439,461 describes a restrictive and/or obstructive implant system for inducing weight loss. In one embodiment, flexible loops are coupled to tissue plications formed in the gastroesophageal junction region of the stomach. An implant, such as a flow restrictive and/or obstructive implant, is passed through the loops 2 and thus retained in the stomach.

In other instances, tissue plications may themselves be sufficient to provide the necessary treatment. For example, the plications may be used to reduce stomach volume or form a flow restriction within the stomach as disclosed in WO 2005/037152 and in Applicants' co-pending application Ser. No. 11/542,457, filed Oct. 3, 2006, U.S. Publication No. 2007-0219571, which is incorporated herein by reference.

Other types of implants may be coupled to such plications or other tissue structures for a variety of purposes. These implants include, but are not limited to prosthetic valves for the treatment of gastro-esophageal reflux disease, gastric stimulators, pH monitors and drug eluting devices that release drugs, biologics or cells into the stomach or elsewhere in the GI tract. Such drug eluting devices might include those which release leptin (a hormone which creates feelings of satiety), Ghrelin (a hormone which creates feelings of hunger), octreotide (which reduces Ghrelin levels and thus reduces hunger), Insulin, chemotherapeutic agents, natural biologics (e.g. growth factor, cytokines) which aid in post surgery trauma, ulcers, lacerations etc. Still other implants might be of a type which might provide a platform to which specific cell types can adhere, grow and provide biologically-active gene products to the GI tract, and/or a platform for radiation sources that can provide a local source of radiation for therapeutic purposes, or provide a platform whereby diagnostic ligands are immobilized and used to sample the GI tract for evidence of specific normal or pathological conditions, or provide an anchor point for imaging the GI tract via cameras and other image collecting devices.

The prior applications listed above, address the desirability of forming tissue plications, pockets or tunnels in a way that regions of serosal tissue (i.e. the tissue on the exterior surface of the stomach) are retained in contact with one another. Over time, adhesions formed between the opposed serosal layers create strong bonds that can facilitate retention of the plication/pocket/tissue over extended durations, despite the forces imparted on them by stomach movement and implanted devices.

Regardless of the application for which a plication is being formed, it is highly desirable to form that plication using steps carried out from within the stomach using instruments passed down the esophagus, rather than using more invasive surgical or laparoscopic methods. The present application describes endoscopic staplers which may be passed transorally into the stomach and used to form serosal-to-serosal plications in a stomach wall.

BRIEF DESCRIPTION OF THE DRAWINGS

FIG. 15A is a cross-sectional side view of the cutting device and a first embodiment of a cutting board.

FIG. 15B is a cross-sectional side view of the cutting device and a second embodiment of a cutting board.

FIG. 16 is a perspective view of the hinged arm assemblies of the stapler head of FIG. 4.

FIG. 26 is a perspective view of the stapler of FIG. 2, with the staple head removed.

FIG. 27A is a plan view of the articulating section of the stapler of FIG. 2, showing the drive fluid lines.

FIG. 27B shows a drive fluid line having an alternate longitudinally expandable shape.

FIG. 28 is a cross-sectional side view of the handle of the stapler of FIG. 2.

DETAILED DESCRIPTION OF THE DRAWINGS

The present application describes endoscopic fastener-applying devices which in preferred embodiments may be passed transorally into the stomach and used to plicate stomach tissue.

In the disclosed embodiments, tissue is drawn inwardly into a vacuum chamber, although tissue may be drawn inwardly using other components (e.g. graspers) that do not involve the use of a vacuum. When a portion the interior stomach wall is drawn inwardly, sections of serosal tissue on the exterior of the stomach are positioned facing one another. The disclosed fastener applying device allows the opposed sections of tissue to be moved into contact with one another, and delivers fasteners that will hold the tissue sections together until at least such time as serosal bonds form between them. Each of these steps may be performed wholly from the inside of the stomach and thus can eliminate the need for any surgical or laparoscopic intervention. After one or more plications is formed, medical devices (including, but not limited to any of the types listed above) may be coupled to the plication(s) for retention within the stomach.

The disclosed embodiments include an optional feature that forms a hole or cut in a plication using the fastener-applying device. This hole or cut might be formed so that a portion of a medical implant may be passed through or linked to the hole/cut, or it may be formed so as to provoke a healing response that will contribute to the strength of the resulting tissue bond.

In the description of the embodiments given below, the fastener-applying devices are described as being staplers, and exemplary methods are given with respect to the formation of plications in stomach tissue. It should be understood, however, that the embodiments described herein include features having equal applicability for applying other types of fasteners, and for applying staples or other fasteners for purposes other than formation of plications. The disclosed embodiments and methods will also find use in parts of the body outside the GI system. Additionally, although the disclosed embodiment features circular stapling and cutting of a concentric hole, modifications are conceivable in which linear stapling can be accomplished, as well as circular or linear stapling without cutting.

Figure 1A:
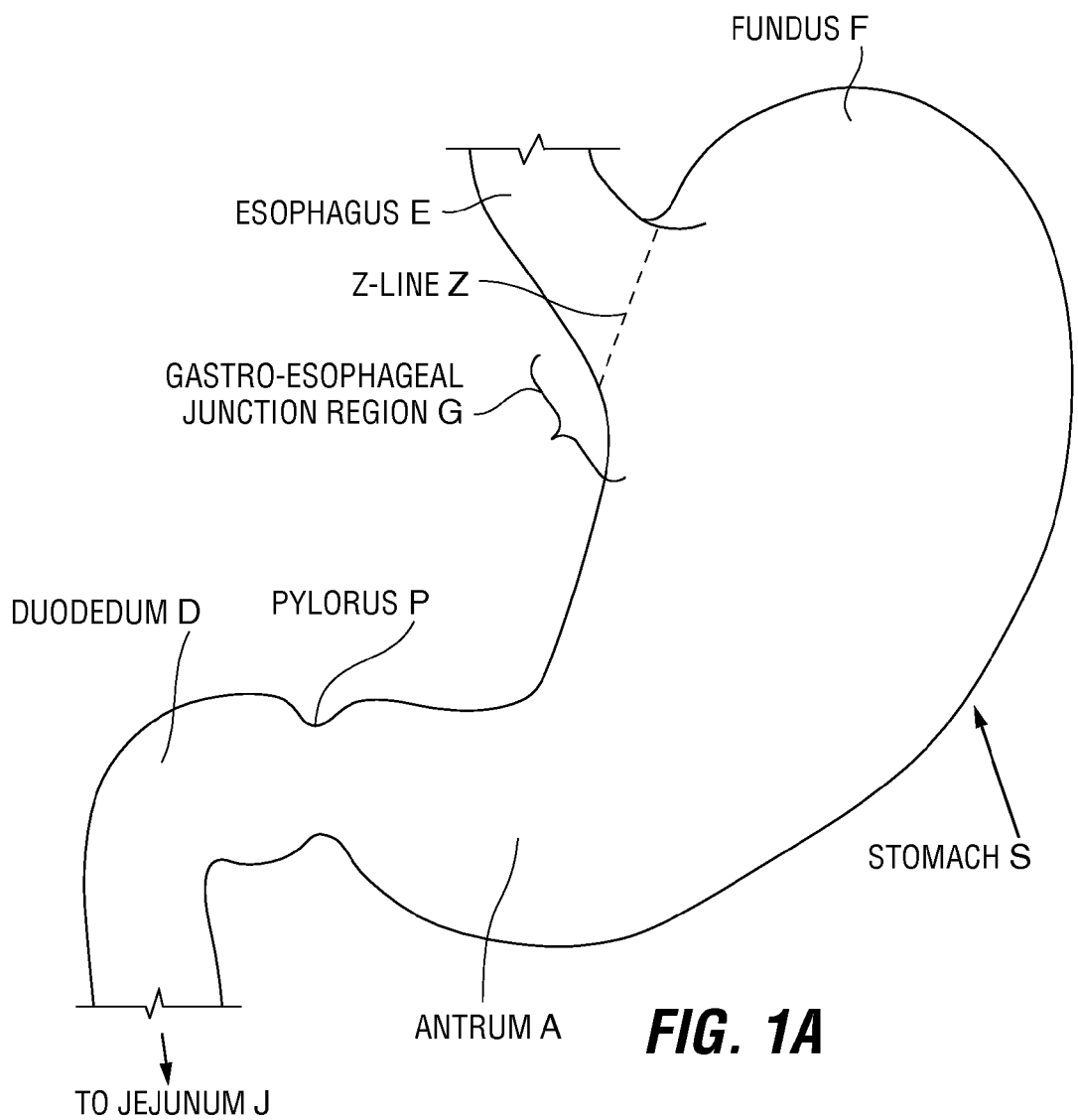
FIG. 1A is a schematic illustration of a human stomach and a portion of the small intestine.
Figure 1B:
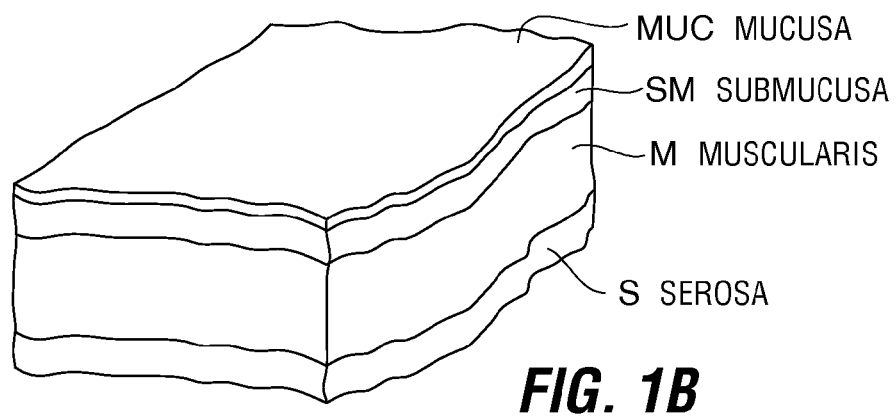
FIG. 1B is a cross-sectional perspective view of a portion of a stomach wall, illustrating the layers of tissue forming the wall.
Figure 2:
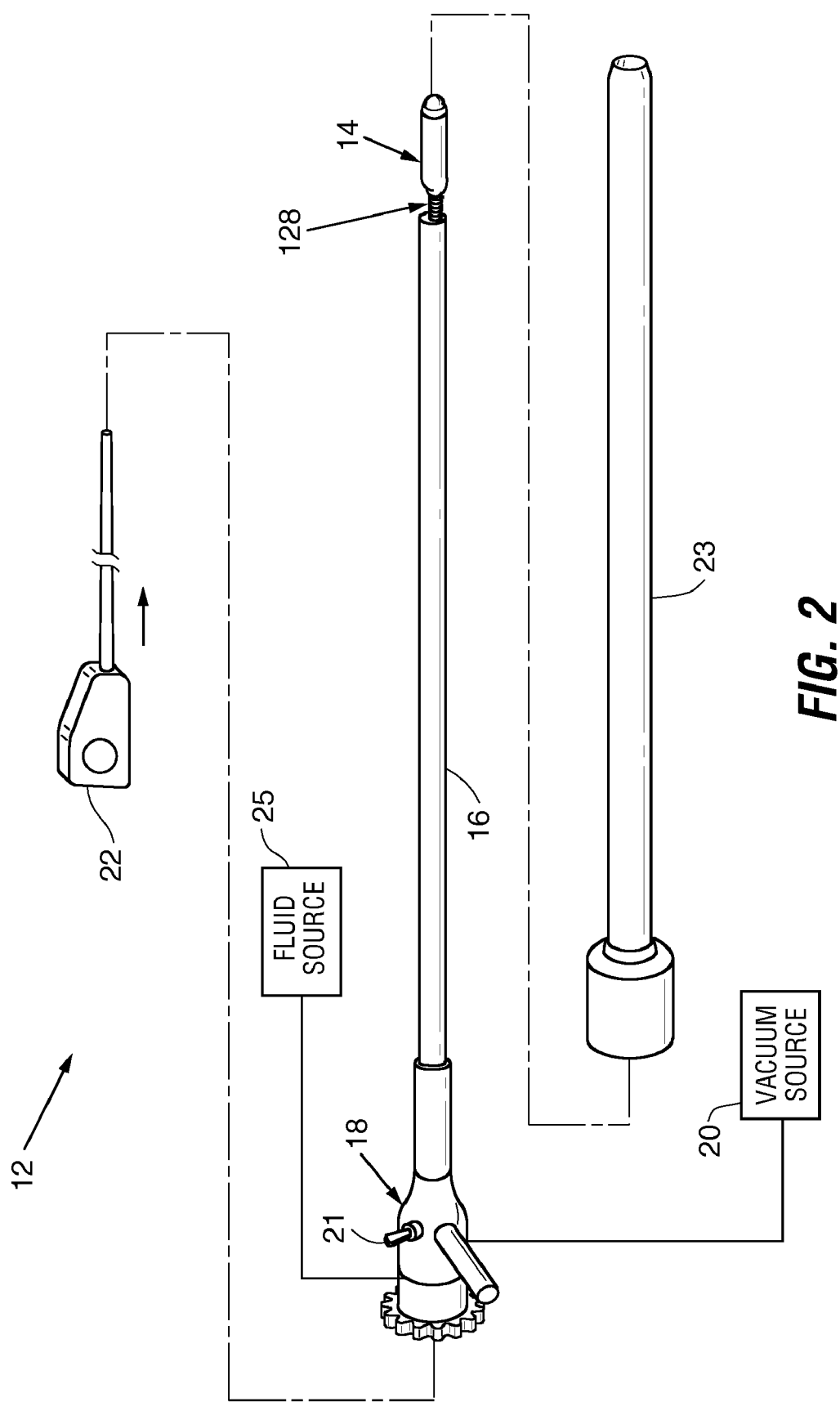
FIG. 2 illustrates an endoscopic stapling system.

FIG. 2 illustrates one embodiment of a system 10 for tissue stapling that is suitable for endoscopic use, as well as surgical or laparoscopic use if desired.

Generally speaking, system 10 includes a stapler 12 having a stapler head 14 positioned on a distal portion of a shaft 16. A handle 18 on the shaft 16 controls articulation of the stapler head 14 and actuation of the tissue acquisition, tissue compression, and stapling functions of the stapler head 14. Vacuum and fluid sources 20, 25 are fluidly coupled to the handle 18 for use in tissue acquisition, compression and stapling as discussed below. The vacuum source 20 may be the "house vacuum" accessible through a coupling on the wall of the operating room, or an auxiliary suction pump. The stapler may include a switch 21 allowing the user to control airflow between the vacuum source and stapler.

The fluid source 25 may be a single source of drive fluid (e.g. water, saline, oil, gas) or multiple sources, but in each case the fluid source preferably includes two actuators separately used to control flow into each of two hydraulic lines (one for tissue compression and one for stapling). An endoscope 22 insertable through a lumen in the shaft 16 permits visualization of the plication procedure. The system may optionally include an overtube, such an endoscopic guide tube 23, having a lumen for receiving the stapler 12.

Figure 3A:
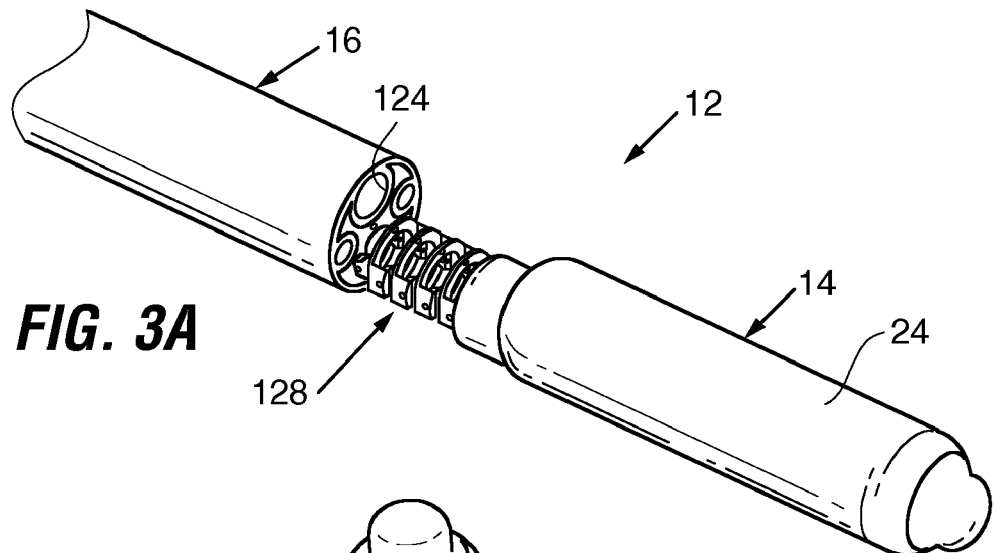
FIGS. 3A-3C are perspective views showing the stapler head of the stapling system of FIG. 2 in three different positions.
Figure 3B:
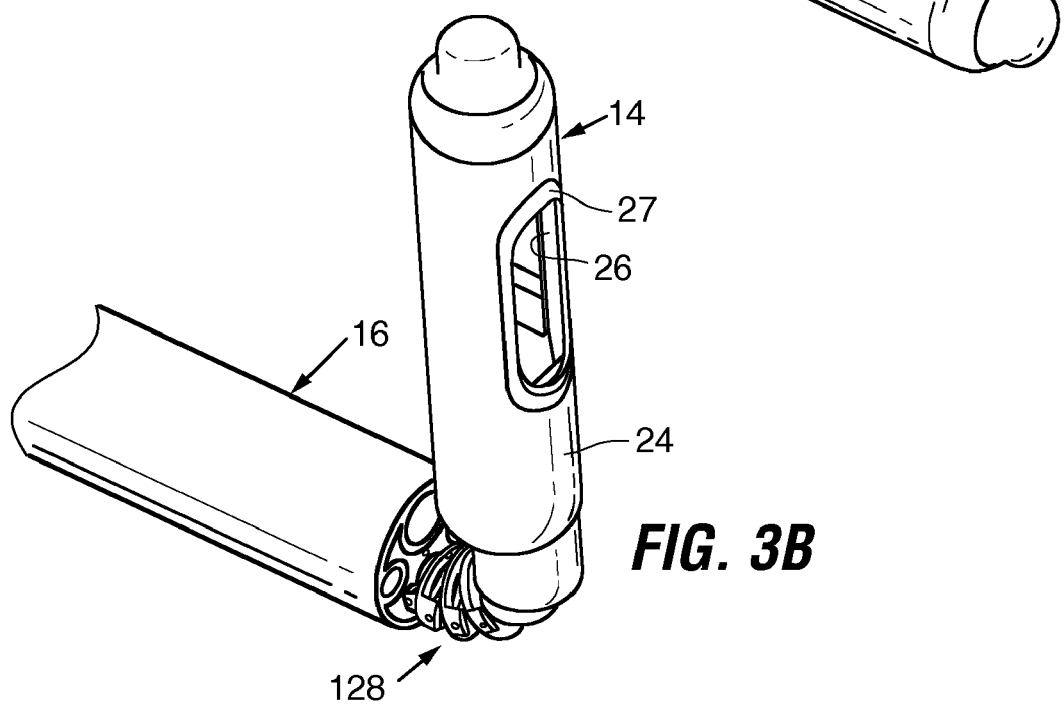

Referring to FIG. 3A, a covering or membrane 24 encloses the stapler head 14 to form a vacuum chamber within the stapler head 14. The side exposed to the tissue to be plicated remains uncovered by the membrane 24 to allow tissue to be drawn into the chamber during use. For example, the membrane 24 may include a side opening 26 as shown in FIG. 3B. Membrane 24 is preferably formed of silicone, elastomeric material, or any other inelastic or elastic flexible or deformable biocompatible material capable of forming a vacuum chamber that will expand in volume to accommodate tissue drawn into the chamber.

At least a portion of the membrane is at least partially transparent. In being at least partially transparent, the membrane is formed of a material, or includes sections of material, that will allow the user to see through the membrane well enough to confirm (via endoscopic observation) that an appropriate volume of tissue has been acquired into the stapler head prior to staple application. The opening 26 may be surrounded by a reinforced section 27 formed of material that will strengthen the area around the opening 26. Reinforced section 27 may be formed of a thicker section of the membrane material, and/or a higher durometer material. Alternatively, reinforcing ribs or other structures or elements may be formed into or onto the membrane material, or embedded in the membrane material.

Stapler Head

The stapler head 14 is designed to have a minimum profile during insertion to the plication site, and to then transform into a much larger profile device having a large internal volume. For example, in one embodiment the vacuum chamber might have an initial internal volume of 0.2 cubic inches, and an expanded volume of 0.6 cubic inches (i.e. the internal chamber volume after subtracting the volume occupied by the stapler head components positioned within the vacuum chamber). This large internal volume allows a large volume of tissue to be drawn into the vacuum chamber and stapled. In this way, the stapler head creates a large plication without requiring invasive techniques for insertion. The unique features of the stapler head allow in situ volumetric expansion of the stapler head using a minimum of motion and force input.

Figure 4:
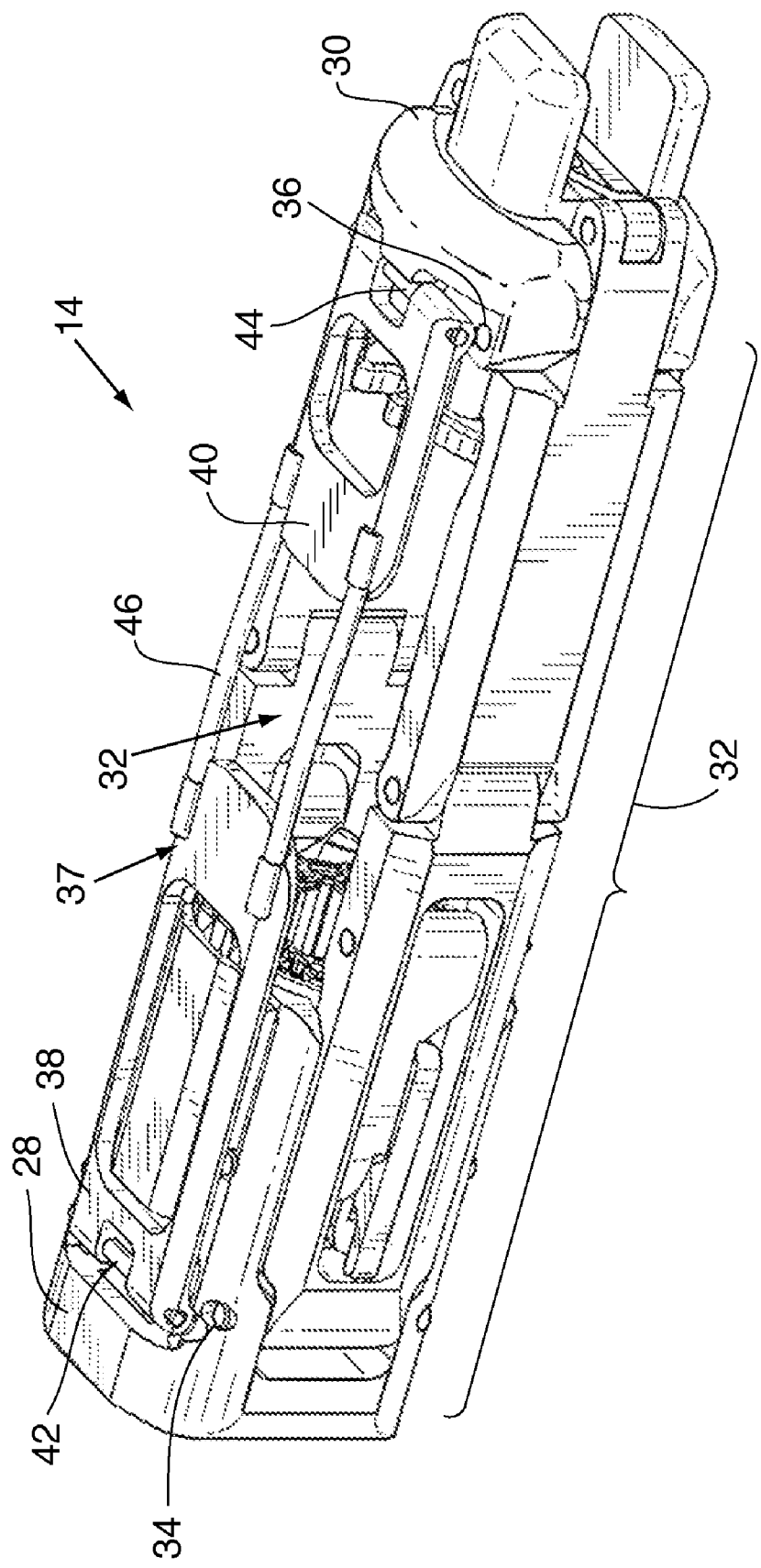
FIG. 4 is a perspective view of the stapler head, with the membrane removed.

Features of the stapler head are shown in FIGS. 4-10. For clarity, the membrane is not shown in these figures. Referring to FIG. 4, stapler head 14 generally includes a first member comprising a proximal staple housing 28, a second member comprising a distal anvil housing 30, and at least one elongate member but preferably a pair of hinged arm assemblies 32.

The staple housing and anvil housing are arranged to allow tissue to be compressed between contact surfaces on each of the staple housing and the anvil housing. In the disclosed embodiment, the contact surfaces are on a staple holding portion of the staple housing and an anvil on the anvil housing.

The arm assemblies 32 extend between the staple housing 28 and anvil housing 30 on opposite sides of the stapler head 14. Proximal and distal pins 34, 36 pivotally couple each arm assembly 32 to the staple housing 28 and the anvil housing 30. An expansion member comprising a membrane raiser 37 also extends between the staple housing 28 and the anvil housing 30. Although the membrane 24 is not shown in FIG. 4, it should be understood that the membrane raiser 37 is positioned opposite the opening 26 (FIG. 3B) in the membrane. In the illustrated embodiment, membrane raiser 37 includes a link 38 pivotally mounted to the staple housing by a pin 42, a corresponding link 40 pivotally mounted to the anvil housing by pin 44, and spring wires 46 coupling the links 38, 40 to one another.

Staple Housing

Figure 5:
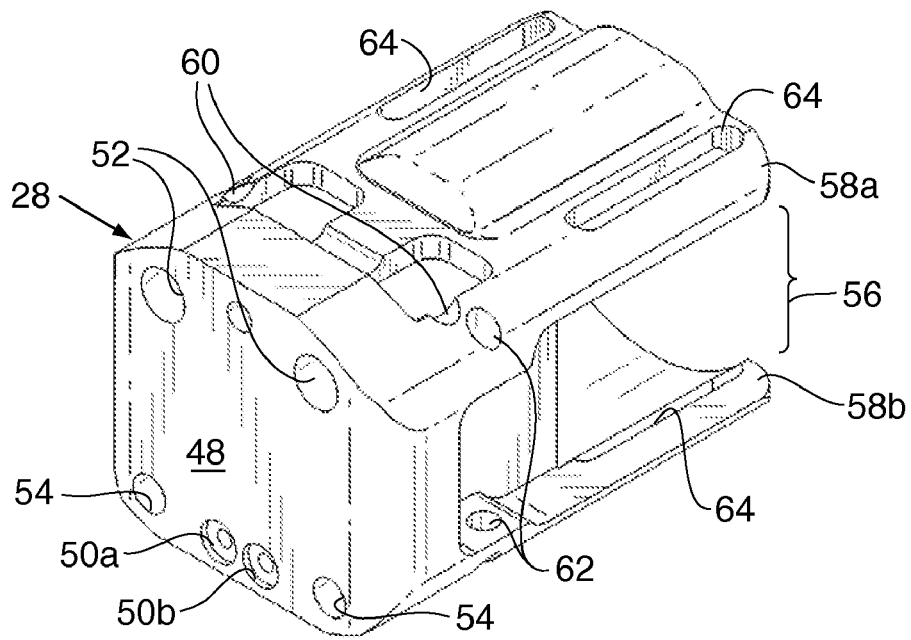
FIG. 5 is a perspective view of the proximal end of the staple housing of the stapler head of FIG. 4.
Figure 6:
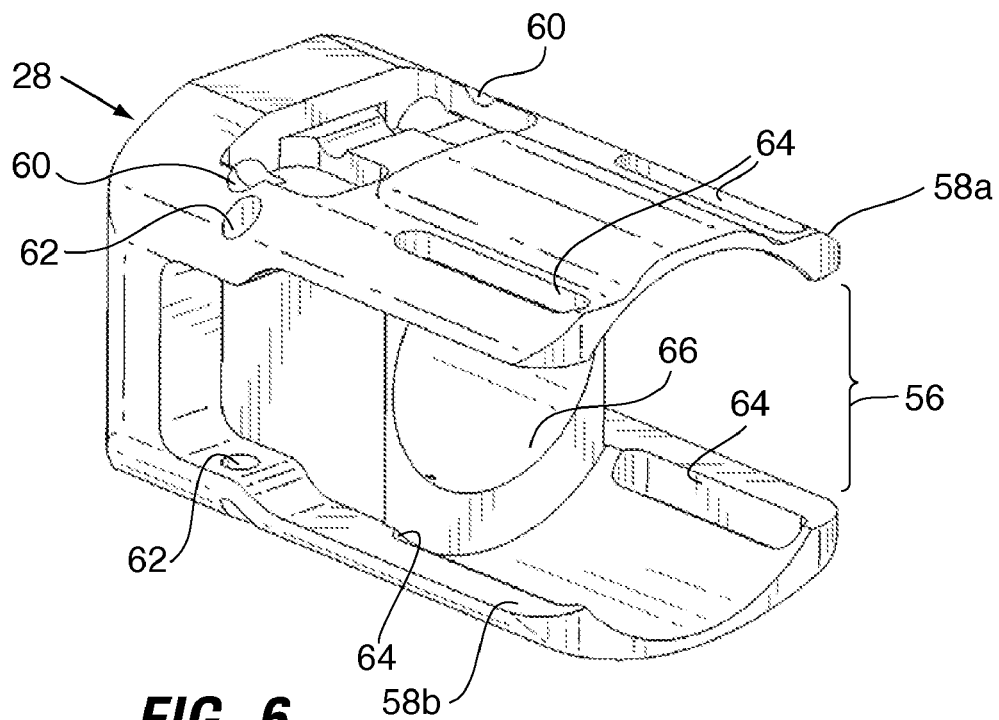
FIG. 6 is a perspective view of the distal end of the staple housing of the stapler head of FIG. 4.

Turning to a more detailed discussion of the stapler head components, the staple housing 28 can be seen separated from other components in FIGS. 5 and 6. As shown in FIG. 5, proximal face 48 of the staple housing includes input ports 50a, 50b through which fluid is directed for hydraulic actuation of the tissue compression, stapling, and optional cutting operations of the stapler head. Seals 51 surround the ports 50a, 50b to minimize fluid leakage.

Vacuum ports 52 are fluidly coupled to a vacuum source 20 (FIG. 2) that is selectively activated to create negative pressure in the vacuum chamber for tissue acquisition. The vacuum ports 52 are connected to the vacuum source 20 by flexible tubing (not shown) in the stapler shaft 16 (FIG. 2). Mounting holes 54 are used to mount the stapler head 14 to the shaft 16.

The staple housing 28 includes upper and lower sections 58a, 58b above and below open side sections 56. The upper section 58a includes a recess 60 within which the pivot pin 42 for link 38 (FIG. 4) is mounted. As best shown in FIG. 6, bores 62 are positioned in the upper and lower sections 58a, 58b to receive pins 34 (FIG. 4) that serve as the proximal pivot points for arm assemblies 32. Guide slots 64 extend longitudinally through the upper and lower sections 58a, 58b.

Referring to FIG. 6, a hydraulic chamber 66 is disposed within the staple housing 28. Within the hydraulic chamber 66 (FIG. 6) is a dedicated hydraulic circuit for driving the tissue compression and stapling functions of the stapler. Chamber 66 is fluidly coupled to the fluid input ports 50a, 50b (FIG. 5). As will be discussed in detail in connection with FIGS. 11A-11D, fluid driven into the hydraulic chamber 66 via input ports 50a, 50b sequentially advances a system of hydraulic pistons (not shown) that act on other components to compress the tissue, and that drive the staples and cutting element through the compressed tissue.

Figure 7:
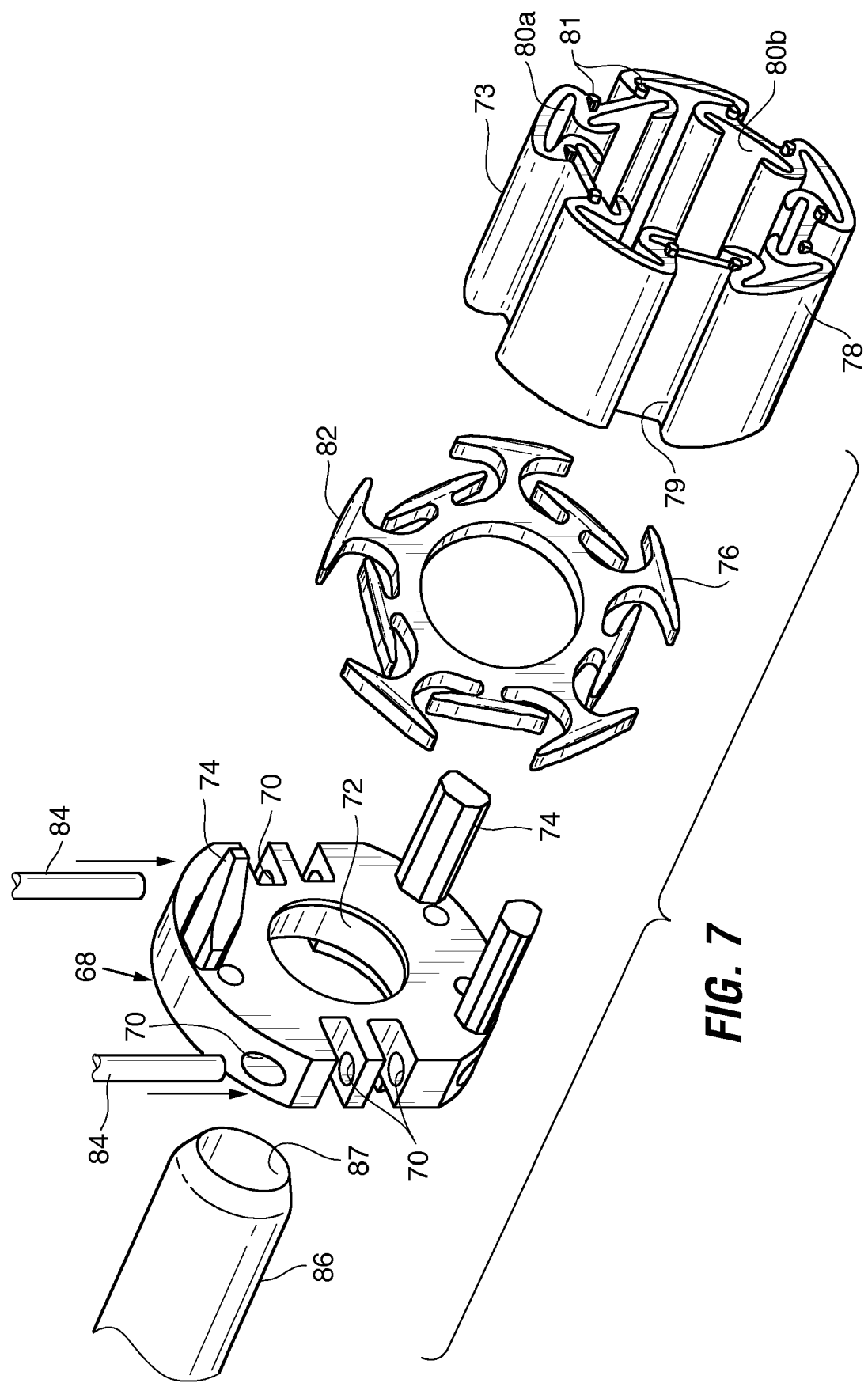
FIG. 7 is an exploded perspective view showing elements advanceable within the staple housing during compression and stapling operations.
Figure 8:
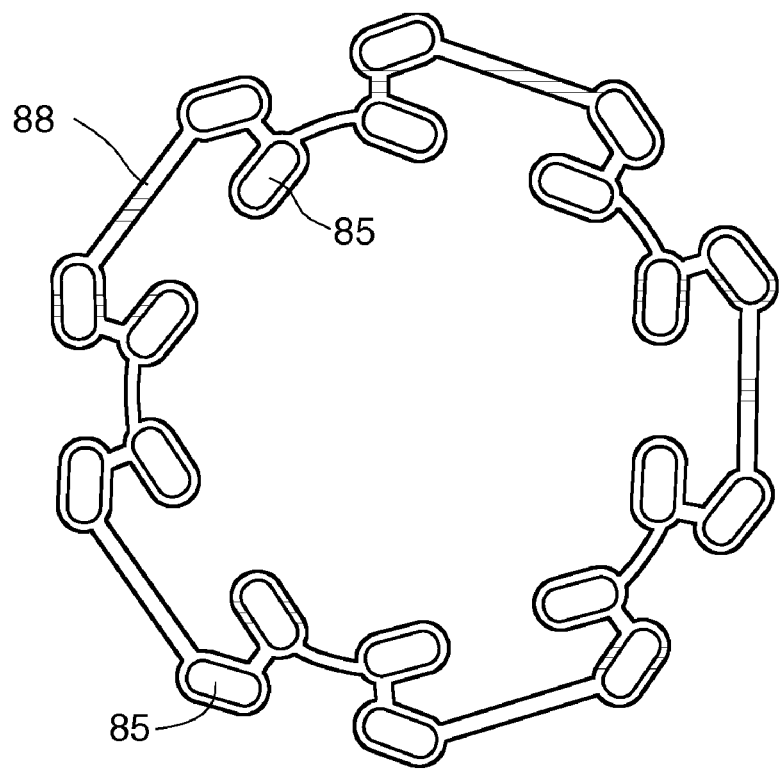
FIG. 8 is a plan view of a staple reinforcement device.

FIG. 7 illustrates components of the stapler head that are driven by the hydraulic system for compression, stapling, and cutting. For clarity, these components are shown separated from the staple housing and from each other. In this discussion, the components that are driven by the hydraulic system will be described. The hydraulic system itself is described in a later section in connection with FIGS. 11A-11D.

In particular, FIG. 7 illustrates a drive member which takes the form of a disk 68 in the staple housing. In the assembled housing, disk 68 is positioned such that it will be pushed distally by a hydraulic compression piston (not shown). The drive member is coupled to the arm assemblies 32, anvil housing, and staple housing so that advancing the drive member distally effects tissue compression by bringing the contact surfaces of the staple housing and anvil housing relatively towards one another.

Figure 10:
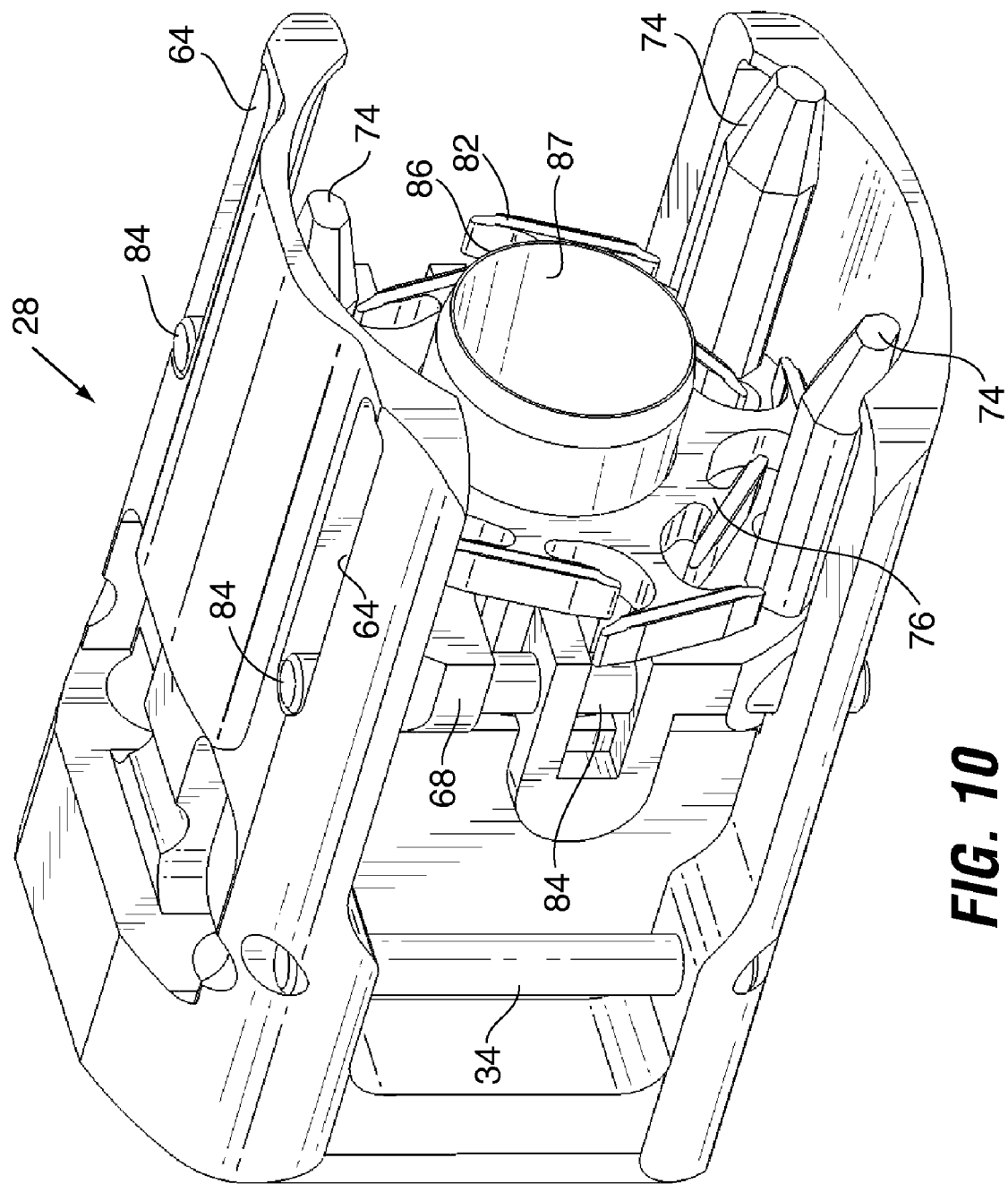
FIG. 10 is a perspective view of the staple housing similar to FIG. 6, but showing some of the elements of FIG. 7 within the housing.

Disk 68 includes mounting bores 70, a central opening 72, and alignment posts 74. Referring briefly to FIG. 10, in the assembled stapler head, disk 68 is coupled to the stapler housing 28 using pins 84 that extend through the housing's guide slots 64 and through mounting bores 70 in the disk 68.

A portion of the staple housing 28 contains staples to be fired into the tissue. The staples are contained within a staple holder on the staple housing. The staple holder may have a number of different configurations. For example, it may be an integral portion of the staple housing, or a separate part mounted or attached to the staple housing, and/or it may be moveable relative to the body of the staple housing to effect tissue compression prior to stapling. In any of these examples, the staple holder may be a removeable/replaceable cartridge, and/or it may be refillable by inserting additional staples into it. In other embodiments, the staple holder may be neither replaceable nor refillable.

In the disclosed embodiment, the staple holder is a removeable staple cartridge 78 that can be replaced with another cartridge after staple filing. In this embodiment, the staple cartridge is moveable relative to the body of the staple housing to compress the tissue prior to staple firing.

Referring again to FIG. 7, staple cartridge 78 is positionable within the staple housing, distal to the disk 68, such that distal advancement of the disk by the compression piston pushes the cartridge distally to compress tissue disposed between the cartridge and anvil. Grooves 79 on the exterior of the cartridge slide over corresponding ones of the alignment posts 74 during insertion of the cartridge into the stapler head. FIG. 10 shows the alignment posts prior to loading of a cartridge into the staple housing. As shown, the alignment posts 74 may have tapered ends to facilitate loading of the cartridge over the posts.

Again referring to FIG. 7, cartridge 78 includes a number of staple locations 80, each housing a staple. The staple cartridge is equipped with bosses 81 to retain a staple line reinforcement device 83 of the type shown in FIG. 8 and disclosed in detail in commonly-owned U.S. application Ser. No. 11/542,457, entitled ENDOSCOPIC PLICATION DEVICES AND METHODS, filed Oct. 3, 2006, and published Sep. 20, 2007 as US 2007-0219571. To summarize briefly, this type of reinforcement device 83 may be a ring or other element positionable against the distal face of the staple cartridge. When the ring is placed on the cartridge, openings 85 in the ring align with prongs of some of the staples in the cartridge. When staples are driven from the cartridge, these prongs pass through associated ones of the openings 85 and capture the ring 83 against the adjacent body tissue.

Figure 9:
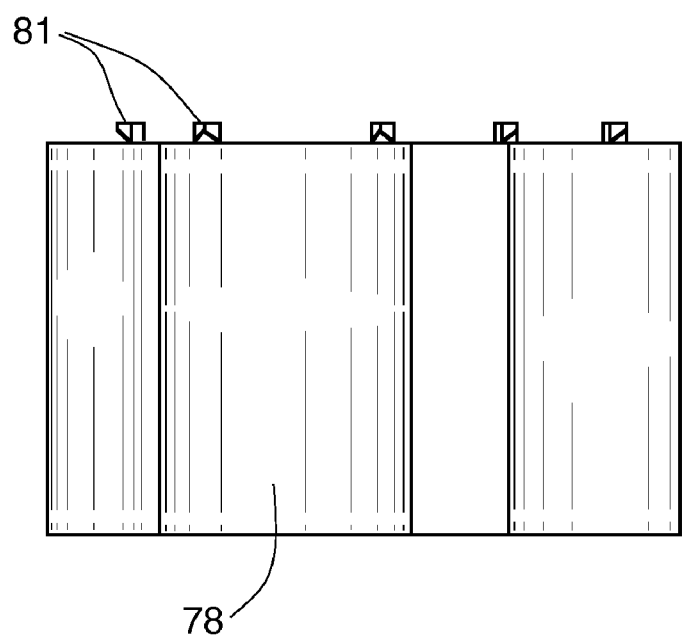
FIG. 9 is a side elevation view of a staple cartridge.

Referring to FIGS. 7 and 9, a number of undercut bosses 81 on the anvil-facing side of the cartridge may be used to lock the reinforcement device 83 in place on the face of the staple cartridge. Other positive shapes, such as mushrooms, hooks, and tilted bosses could be used to accomplish the same end. Negative shapes, such as pockets or grooves formed into the surface of the cartridge, may also be employed to engage corresponding features on the reinforcement device 83. As another alternative, the reinforcement device may be held in place on the cartridge using adhesives.

A cutter element 86 extends through the central opening 72 (FIG. 7) of the disk 68. The cutter element is shown as a tubular punch having a sharpened wall and a lumen 87, but may be provided in alternative forms. A staple pusher 76 is mounted to the cutter element, distally of the disk as can be seen in the assembled view of FIG. 10. Staple pusher 76 includes pusher elements 82 proportioned to slide into the cartridge's staple locations 80 as the staple pusher 76 is advanced into the staple cartridge 78, thus driving the staples from the cartridge. A hydraulically-driven staple piston (not shown in FIG. 7) in the hydraulic chamber 66 is coupled to the cutter element 86 such that advancement of the stapler piston advances the staple pusher 76 and cutter element 86 in a distal direction.

Fluid Drive System

Figure 11A:
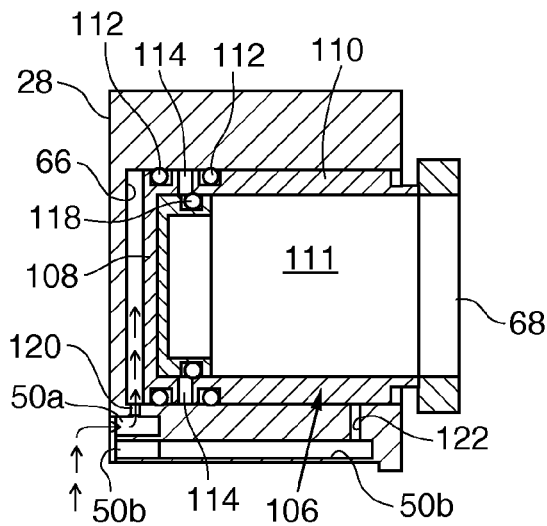
FIGS. 11A-11D are a series of schematic representations of the hydraulic chamber and pistons, illustrating operation of an exemplary hydraulic system during tissue compression and stapling.
Figure 11B:
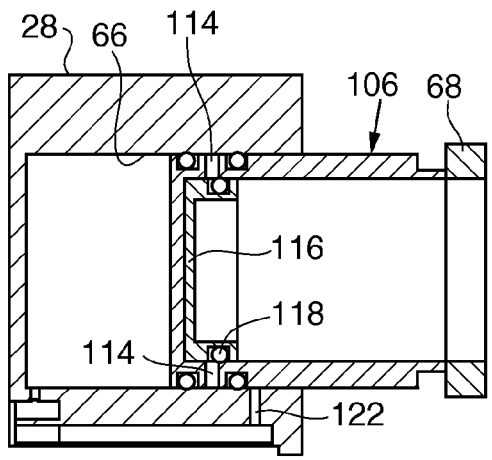

The fluid drive system used to actuate compression, stapling and cutting may be configured in various ways. The following paragraphs describe one exemplary configuration for the fluid drive system, which in this embodiment is a hydraulic system. FIGS. 11A and 11B schematically show the fluid flow in the hydraulic chamber 66 of the staple housing 28 during both compression and stapling stages of actuation. Referring to FIG. 11A, compression piston 106 is disposed within hydraulic chamber 66. Disk 68 (also shown in FIGS. 7 and 10) is positioned in contact with or slightly distal to piston 106. Compression piston 106 is generally cup-shaped, having a rear wall 108 and a side wall 110 enclosing an interior 111. O-ring seals 112 are spaced-apart on a proximal portion of the side wall 110. Channels 114 are formed through the side wall 110, between the o-ring seals 112.

A second piston, referred to as the staple piston 116, is positioned in the interior 111 of compression piston 106, against the rear wall 108. Although not shown in FIGS. 11A-11D, cutting element 86 (FIG. 7), with the staple pusher 76 thereon, is positioned in contact with or slightly distal to the staple piston 116. An o-ring seal 118 surrounds a portion of the staple piston 116 that is distal to the channels 114 in the compression piston.

Figure 11C:
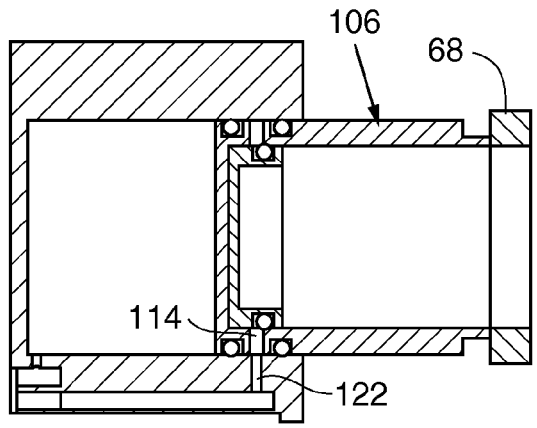
Figure 11D:
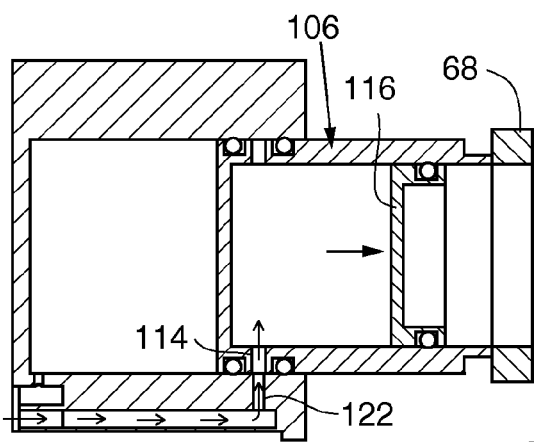
Figure 11E:
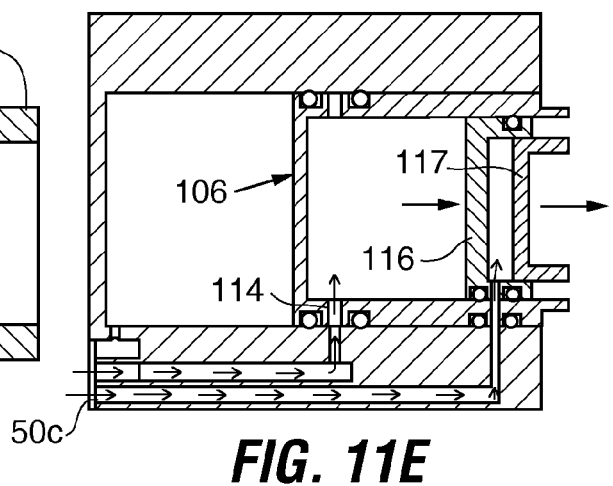
FIG. 11E is similar to FIG. 11D and shows an alternative piston configuration.

A first fluid channel 120 extends from fluid port 50a in the stapler housing 28 to a proximal section of the hydraulic chamber 66. A second fluid channel 122 extends from fluid port 50b in the stapler housing to a more distal section of the hydraulic chamber 66. Fluid flow from port 50a and fluid channel 120 against the compression piston cylinder is shown in FIG. 11A. Fluid pressure within the hydraulic chamber 66 advances the compression piston 106, with the stapler piston 116 within in it, in a distal direction. FIG. 11B shows the compression piston 106 approaching the end of its travel. Once the compression piston reaches the end of its travel as shown in FIG. 11C, channel 114 in the compression piston 106 aligns with channel 122 in the housing, allowing fluid introduced through fluid port 50b to enter the interior of the compression piston 106 via channel 122. The fluid entering the interior of the compression piston drives the staple piston distally as shown in FIG. 11D. In an alternative embodiment shown in FIG. 11E, a third piston 117 is provided for separately driving the cutting element 86. In this embodiment, fluid introduced into a third drive fluid port 50c causes advancement of the third piston 117. The pistons 106, 116 and 117 and associated fluid paths may be arranged so that fluid cannot enter the interior of the stapler piston to advance the cutting piston 117 until compression piston 106 has traveled to the tissue-compression position and stapler piston 116 has in turn traveled to the stapling position.

Figure 12:
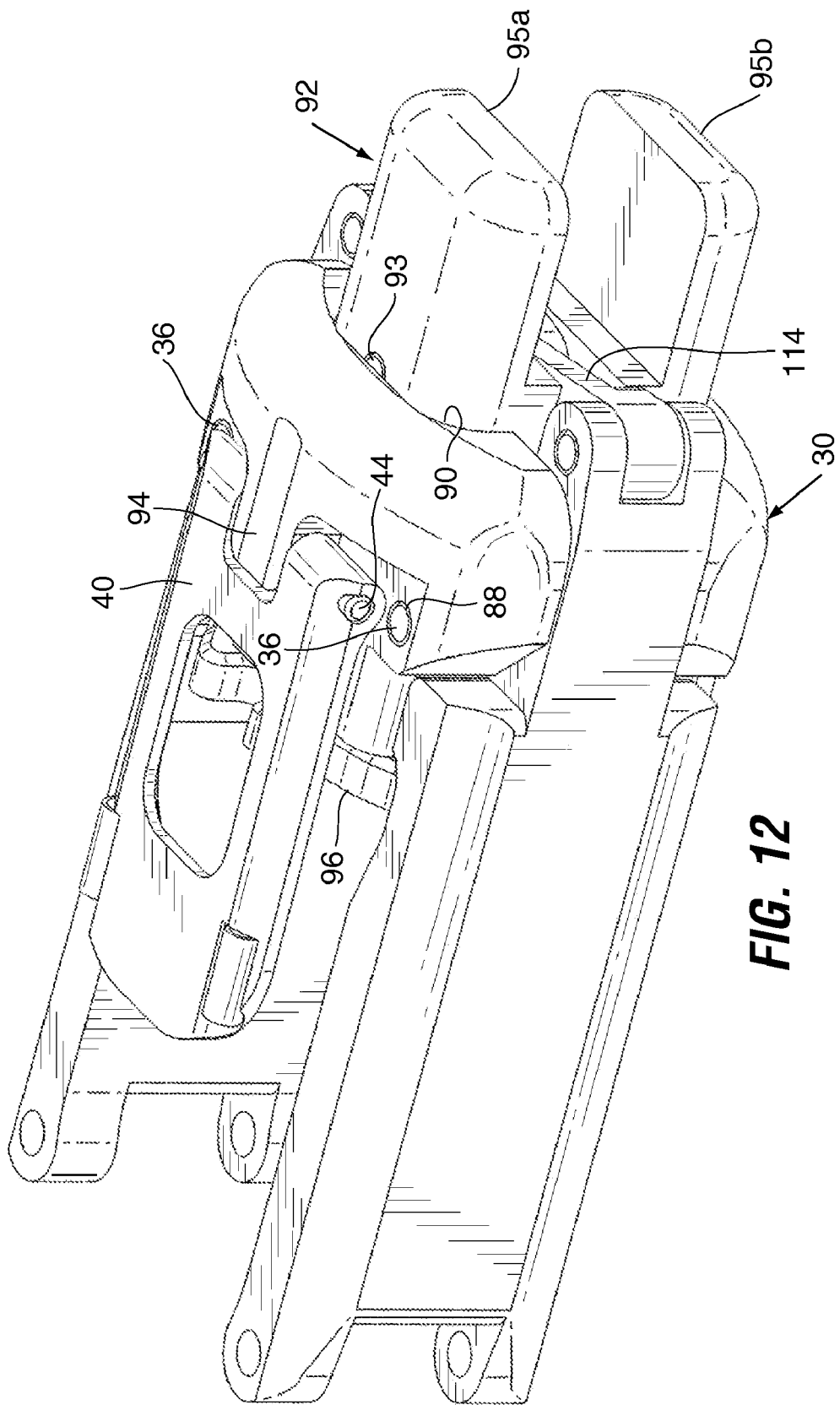
FIG. 12 is a perspective view of the anvil housing of the stapler head of FIG. 4.

The anvil housing (identified by numeral 30 in FIG. 4) will next be described with reference to FIG. 12. The anvil housing 30 includes mounting bores 88 for receiving pivot pins 36 at the distal end of the hinged arm assemblies 32. The upper section of the anvil housing 30 includes a section 94 through which the pivot pin 44 for link 40 (FIG. 4) is mounted.

A central bore 90 extends longitudinally through the anvil housing 30. An anvil support 92 is longitudinally slidable within the bore. Both the bore 90 and the anvil support 92 are preferably formed to have non-circular cross-sections (such as the illustrated rectangular cross-section) with flat bearing surfaces to prevent rotation of the piston within the bore.

Figure 13:
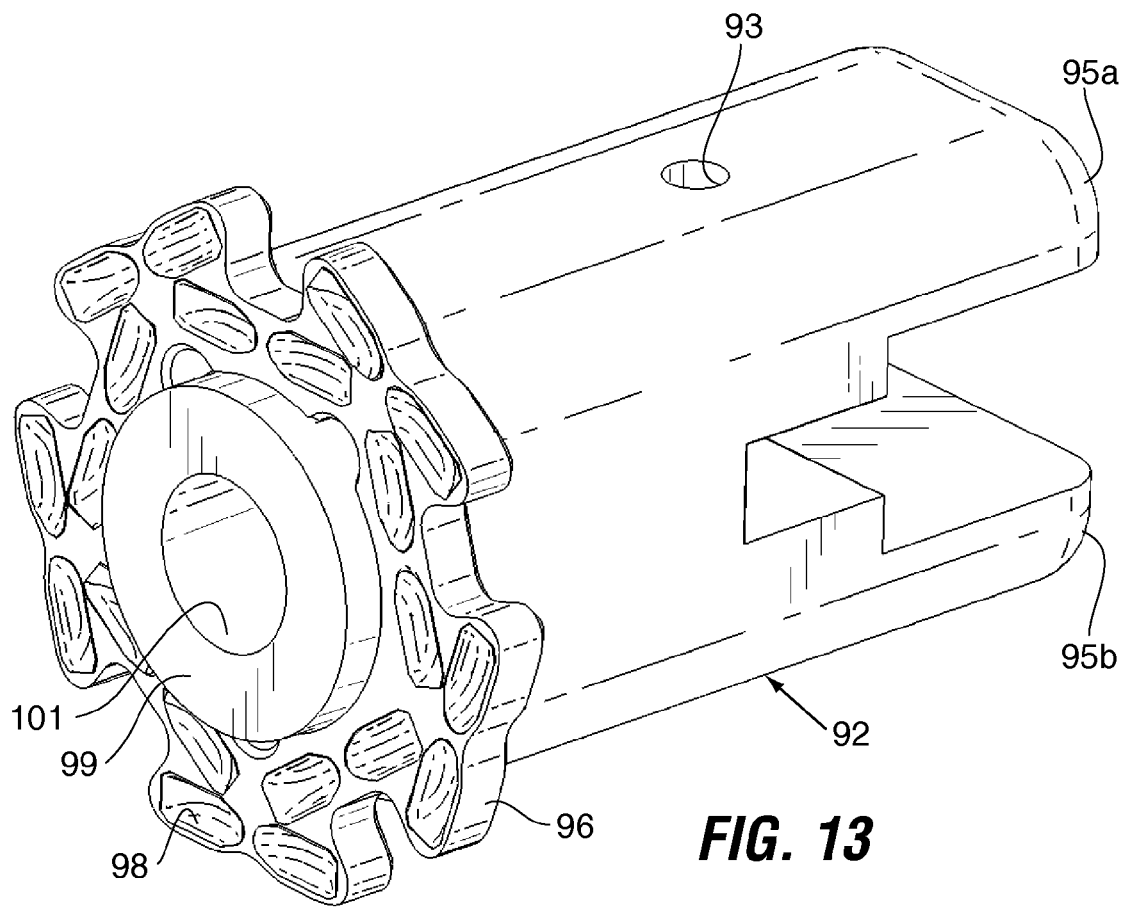
FIG. 13 is a perspective view of the anvil support.
Figure 14:
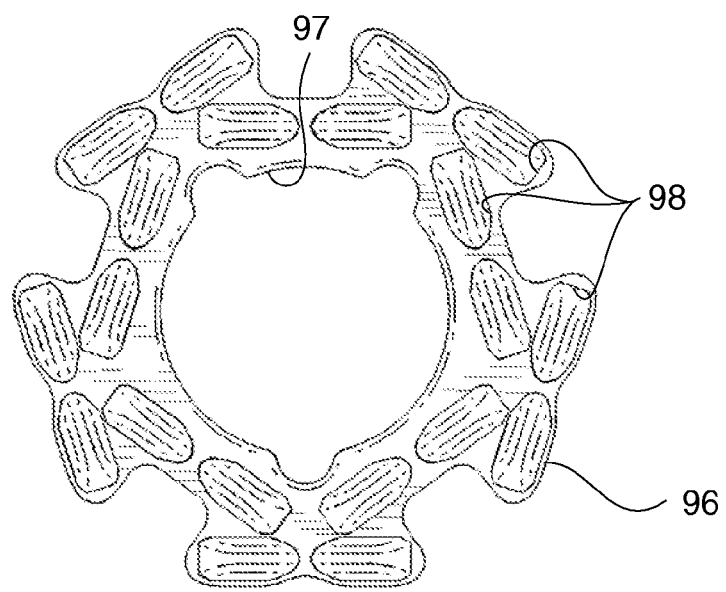
FIG. 14 is a plan view of the anvil.

FIG. 13 shows the anvil support 92 separated from the anvil housing 30. The distal portion of the anvil support 92 is split into upper and lower plates 95a, b. Plate 95a has a bore 93 axially aligned with a similar bore in plate 95b. The proximal portion of the anvil support 92 carries the anvil 96. As shown in FIG. 14, anvil 96 includes a plurality of indentations 98 positioned such when staples are driven from the staple cartridge, each staple leg engages one of the indentations, which causes the staple leg to fold. A central opening 97 extends through the anvil 96 and is contiguous with a lumen in the anvil support 92.

The anvil 96 and the staple cartridge 78 (FIG. 7) are the two parts of the stapler head which exert force on the tissue to be stapled. As shown in FIGS. 9 and 14, the preferred anvil and cartridge are designed to use a minimal amount of material surrounding the indentations 98 of the anvil 96 and the staple locations 80 of the cartridge 78—so that the amount of anvil/ cartridge surface area contacting the tissue is as small as possible. When subjected to a constant force, a smaller footprint will damage less tissue than would a larger footprint, since a smaller area of tissue is squeezed between the anvil and cartridge. However, the tissue that does get squeezed experiences more pressure from the given force because the force is distributed over a smaller area. In other words, the minimized footprint creates more pressure on the tissue with less force. This is advantageous from a mechanical standpoint because the stapler head need not supply or withstand as much force as would be needed with a larger-footprint cartridge and anvil.

Referring to FIG. 7, in the illustrated embodiments, the staple cartridge 78 has an outer wall that tracks the contours of the staples housed within it, thus forming a number of pedals 73 surrounding the outer staple positions or slots 80a, with the grooves 79 disposed between the pedals, adjacent to the inner staple positions 80b. Rather than providing each staple position to be fully surrounded by cartridge material, the staple positions 80a, 80b preferably each include a back wall 71a and a retaining element attached to the wall and positioned to retain a staple between the retaining element and the back wall. In FIG. 7, the retaining element comprises a pair of wings 71b that curve inwardly from the back wall 71 to define a slot that is sufficiently bounded to retain a staple within the staple position, but that is preferably not bounded around its full circumference. The anvil has a similar pedal arrangement, as shown in FIG. 13.

Referring again to FIG. 13, a plate 99 is positioned on the anvil 96 such that the distally-advancing cutting element 86 will advance into contact with the plate 99 during tissue cutting. In one embodiment, the plate 99 may be seated within the opening 97 in the anvil. The plate 99, which will also be referred to as the "cutting board", has a hole 101 in it which relieves the pressure of the captured tissue and prevents hydraulic locking, a condition in which the punch and plate create a closed volume. If it is desired to move the cutting element 86 after contact is made, pressure will increase inside this closed volume and it will resist further motion. This may prevent or adversely affect tissue cutting.

The cutting board is preferably designed so as to not serve as a hard stop against advancement of the cutting element 86. If the cutting element 86 is stopped by the cutting board, the stapling piston will also be stopped and incomplete staple formation may result. Therefore, it is preferred that the cutting element 86 is allowed to penetrate or displace the cutting board during and after the tissue is cut.

FIGS. 15A and 15B illustrate the cutting element 86 advanced into contact with two different embodiments of cutting boards. In the FIG. 15A embodiment, the material of cutting board 99a is a relatively soft material, such as an elastomeric silicone, which is cut by the advancing cutting element as shown. This material allows the sharp distal end of the cutting element to move into the cutting board during the final stage of staple formation. In the FIG. 15B embodiment, the cutting board 99b can be made of a harder material positioned with a compressible object such as an elastomeric spring 99c behind it. In the figure, this spring is an o-ring. Advancement of the cutting element 86 against the cutting board 99b causes the cutting board to be displaced distally against the spring 99c. The advancing cutting element 86 experiences increasing resistance as the o-ring is compressed. Other spring shapes and materials, such as coiled wire, spring washers and leaf springs can be used to achieve the same result. The chamfer 99d on the surface of the cutting board 99b may help to align the cutting element 86 as it is forced into contact with the cutting board.

Arm Assemblies

Following is a discussion of the features of the arm assemblies 32. FIG. 16 shows the arm assemblies 32 separated from the other elements of the stapler head. In general, each arm assembly has a first arm section pivotally coupled to the staple housing and a second arm section pivotally coupled between the first arm section and the anvil housing. While not present in the illustrated embodiment, additional arm sections may be positioned between the first and second arm sections.

Each arm assembly includes a proximal arm 100 and a distal arm 102 joined to one another to form a hinge 104. Each of the proximal arms 100 has a longitudinal cutout 108 and a spreader arm 110 pivotally mounted within the cutout 108. The distal end of each spreader arm 110 includes a bore 112. Pin 84 is positioned within the bore 112. As disclosed in connection with FIG. 10, this pin 84 extends through the disk 68 and has ends that ride within the slots 64 (FIG. 6) on the lower and upper sections of the stapler housing. Longitudinal movement of the disk 68 within the stapler housing will thus advance the pins 84 within their corresponding slots 64, causing the spreader arms 110 to pivot relative to the pins 84 and to thus drive the arm assemblies 32 outwardly. Additional specifics concerning movement of the arm assemblies 32 is set forth in the section entitled Stapler Head Operation.

Distal arms 102 of the arm assemblies include pins 36 which, as discussed, are pivotally mounted to the anvil housing 30 (FIG. 4). A pair of drive links 114 are provided, each of which has a first end pivotally attached to a corresponding one the distal arms 102 and a second end pivotally coupled to a common pin 116. In the assembled stapler head, pin 116 is positioned in the bores 93 of the upper and lower plates 95a, 95b of the anvil support (see plates 95a, b in FIG. 12). As detailed in the Stapler Head Operation section below, when the spreader arms 110 drove the arm assemblies 32 outwardly, drive links 114 act on the pin 116 to push the anvil support in a proximal direction, causing the anvil to advance proximally towards the staple cartridge.

Stapler Head Operation

The following discussion centers on the manner in which the arm assemblies function to expand the vacuum chamber and to compress tissue that has been drawn into the chamber using suction. As an initial step preceding chamber expansion, the stapler head is positioned with the opening 26 in the membrane 24 in contact with tissue at the location at which plication creation is desired. Vacuum source 20 (FIG. 2) is activated to apply vacuum to the inside of the vacuum chamber defined by the membrane. Tissue in contact with the opening 26 (FIG. 3B) will be drawn into the vacuum chamber between the staple housing 28 and the anvil housing 30. After the tissue is drawn in, the stapler profile is changed, expanding the volume of the chamber within the membrane.

Figure 17:
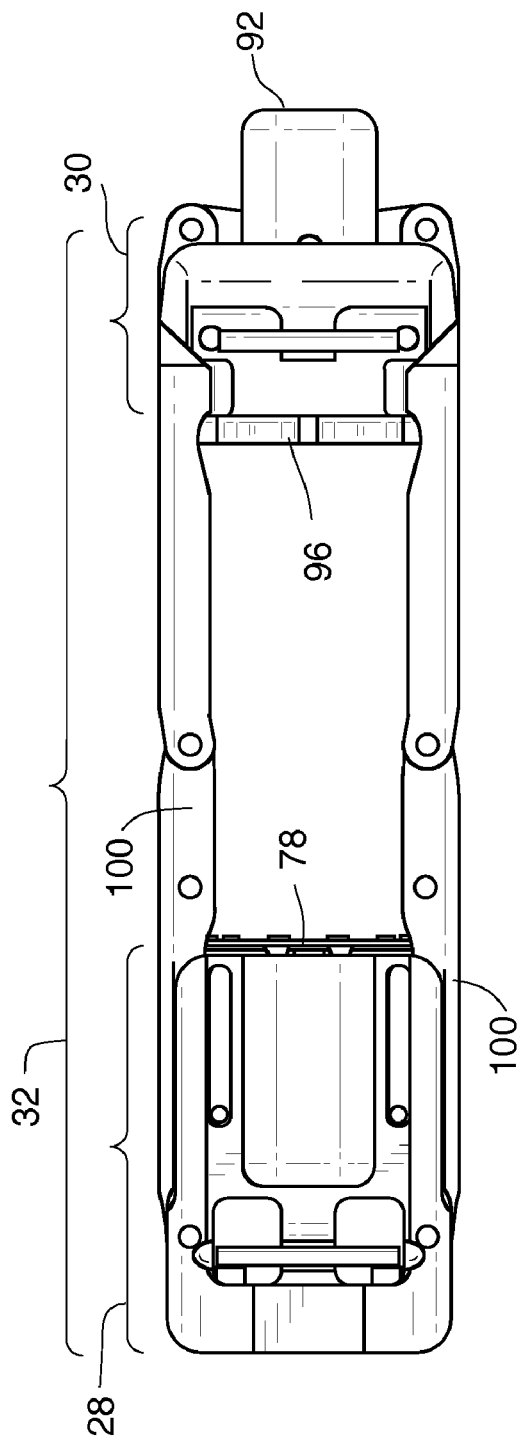
FIG. 17 is a top plan view of the stapler head of FIG. 4 in the streamlined position for introduction into the body. Both the membrane and the membrane raiser are not shown for purposes of clarity.
Figure 18:
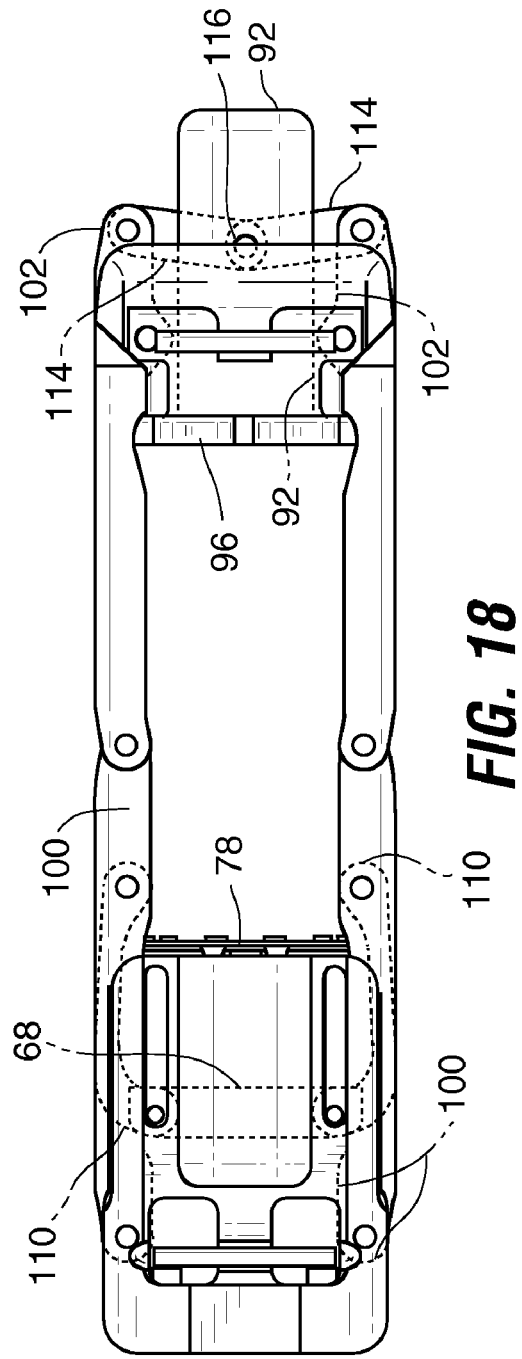
FIG. 18 is similar to FIG. 17 and illustrates hidden features of FIG. 17.
Figure 19:
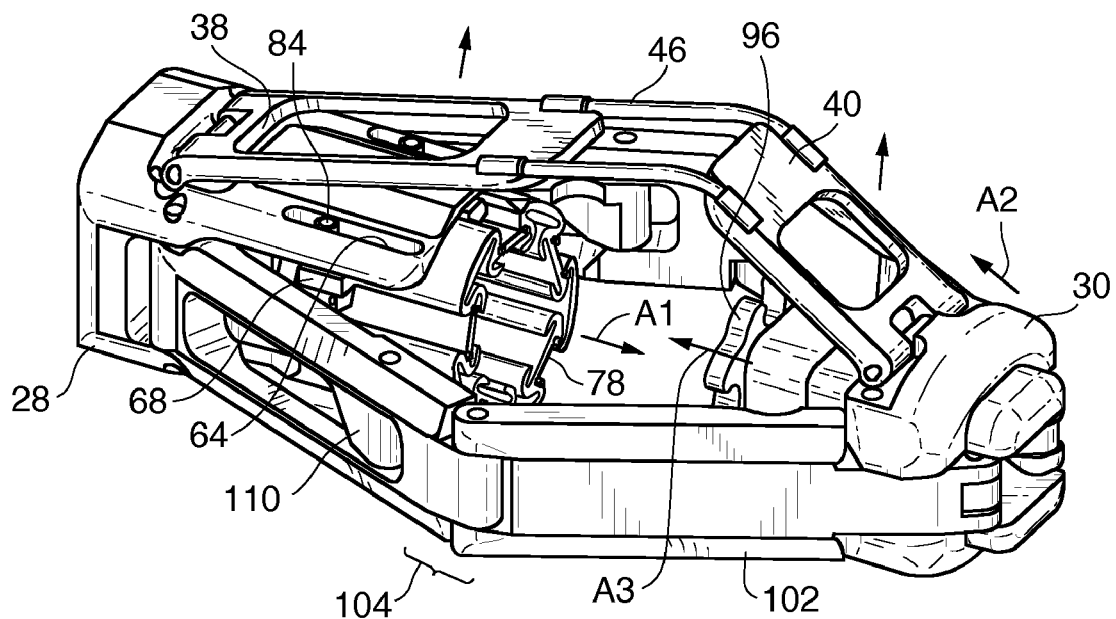
FIG. 19 is a perspective view of the stapler head in an intermediate, partially expanded, position.

The streamlined position of the stapler head 28 prior to expansion is shown in FIGS. 4, 17 and 18. In particular, the hinged arm assemblies 32 and membrane raisers 37 are in generally straight orientations. The proximal arms 100 serve as the drive arms for chamber expansion and tissue compression. Motion of these arms is initiated when water under pressure is forced into the hydraulic circuit of the staple housing. Referring to FIG. 19, the fluid pressure advances disk 68 (by action of the compression piston 106, not shown in FIG. 19). Disk 68 in turn pushes the staple cartridge 78 toward the anvil 96 as shown in FIGS. 19-21, causing the staple cartridge 78 to extend further from the staple housing 28.

Both the disk 68 and the arm spreaders 110 are coupled to the pins 84. For this reason, the longitudinal movement of the disk 68 within the stapler housing 28 will carry the pins 84 distally within their corresponding slots 64. The arm spreaders 110 will consequently pivot relative to the pins 84, driving the proximal arms 100 outwardly. Outward movement of proximal arms 100 at hinge 104 causes the distal arms 102 to also pivot outwardly at hinge 104, forming an angle between the proximal and distal arms 100, 102. Naturally, formation of the angle between the arms 100, 102 shortens the effective length between the remote ends of the arms, causing the distal pins 36 of the distal arms 102 to carry the anvil housing 30 towards the staple cartridge. The pivoting movement of the distal arms 102 further causes drive links 114 to act on pin 116 to push the anvil support in a proximal direction. This moves the anvil support relative to the anvil housing in a proximal direction at the same time the anvil housing is also moving proximally.

Figure 20:
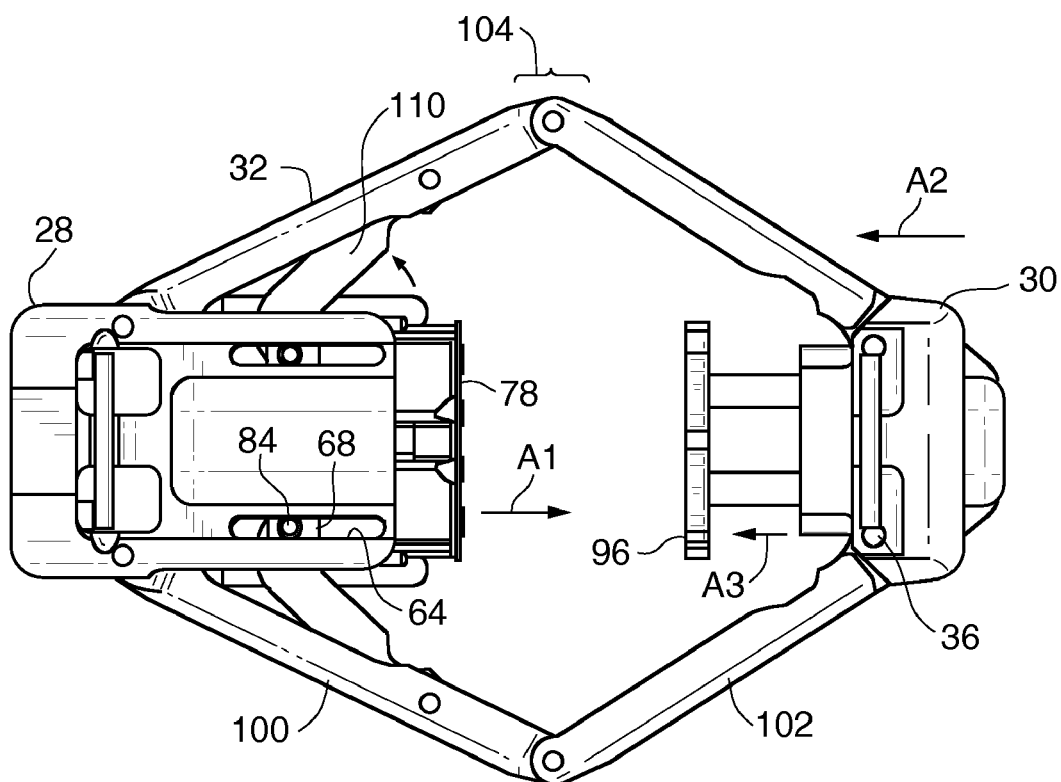
FIG. 20 is a plan view similar to FIG. 17 but showing the stapler head in the intermediate position.
Figure 21:
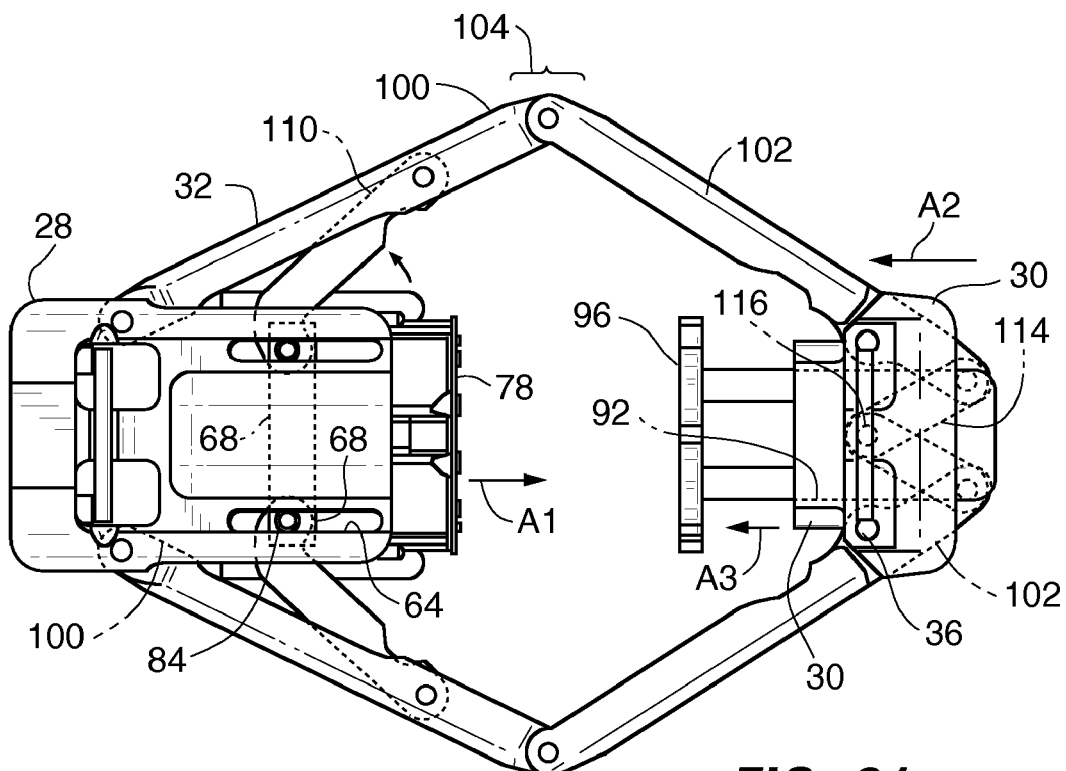
FIG. 21 is similar to FIG. 20 and illustrates hidden features of FIG. 20.

In essence, one motion, that of the hydraulically driven compression piston, creates at least three motions, illustrated by arrows A1, A2 and A3 in FIGS. 19-21. These three motions include: the staple cartridge 78 moving relative to the staple housing in a direction towards the anvil 96 (arrow A1), the anvil housing 30 moving toward the staple housing 28 (arrow A2) and the anvil 96 itself moving relative to the anvil housing 30 in a direction towards the cartridge (arrow A3). This compound motion of the anvil toward the staple cartridge enables a small displacement of the compression piston to quickly compress tissue in the grip of stapler. The multiplication of motion also enhances force transmission between the two housings by keeping the angle at hinge 104, between the proximal (driven) arm and the distal (drive) arm, as large as possible.

The relative motion of the two housings 28, 30 toward each other also drives upward links 38, 40 and their interconnecting spring wires 46 on the top of the stapler head 14. Together, the links and spring wires raise the top of the membrane, creating more volume to accommodate expansion of the tissue during compression.

Figure 22:
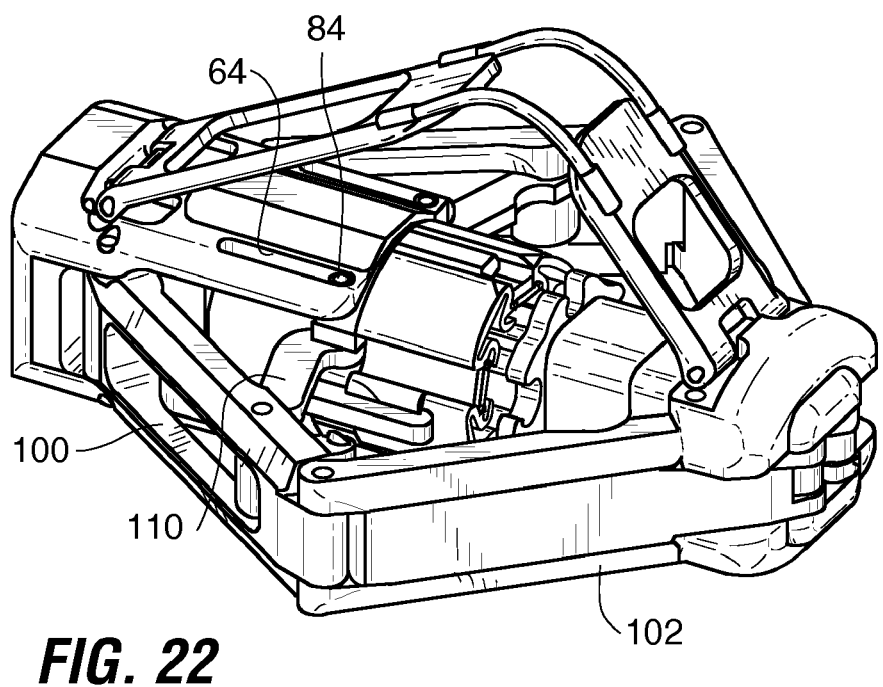
FIG. 22 is a perspective view of the stapler head in a fully expanded, full compression position.
Figure 23:
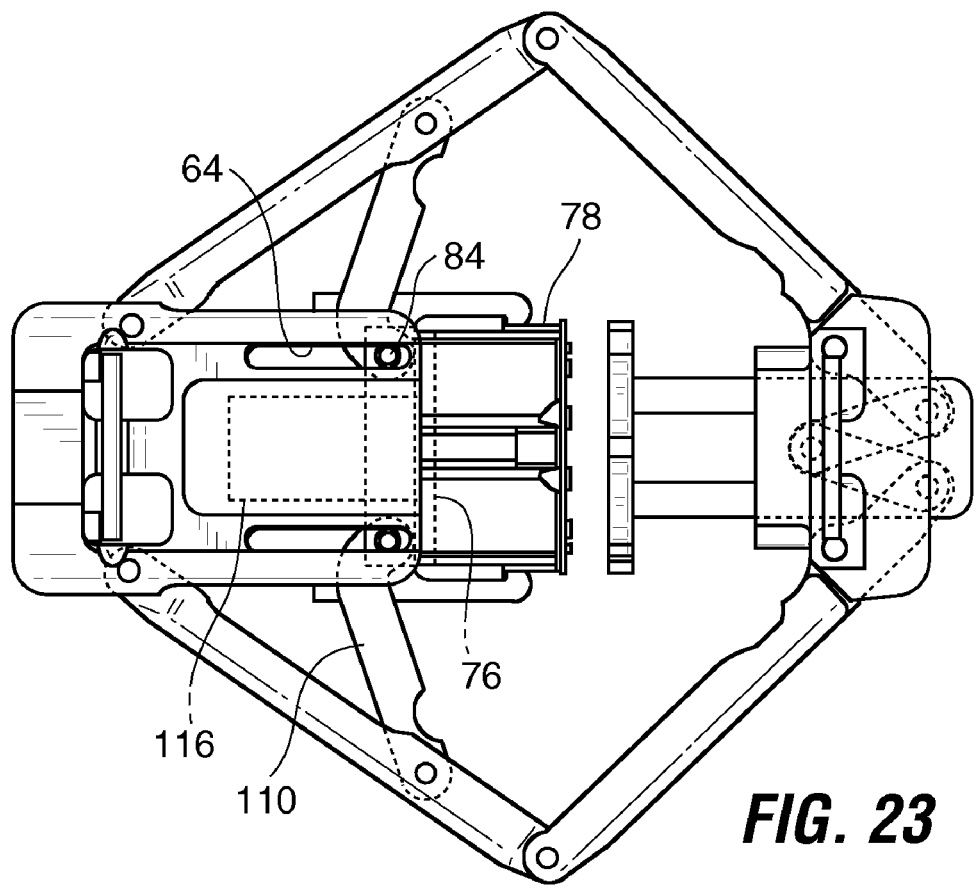
FIG. 23 is a plan view similar to FIG. 20 but showing the stapler head in the full compression position.
Figure 24:
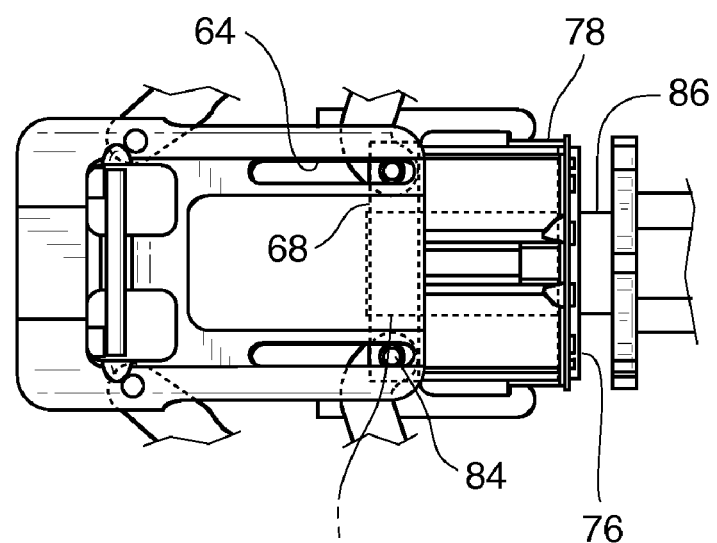
FIG. 24 is similar to FIG. 23 and illustrates hidden features of FIG. 24.

Compression of the tissue is halted when the pins 84 traveling in slots 64 in the staple housing 28 reach the limit of travel, as shown in FIGS. 22-24. Thus, the slots and associated components are dimensioned to set the desired separation distance between the tissue contact surfaces on the stapler side and the anvil side of the stapler head. Exemplary separation distances for use in stomach wall plications might include approximately 0.06-0.07 inches (e.g. for use with staples having legs of 5.5 mm length) or 0.109 inches for 6.5 mm leg length staples. Application of additional pressure into the hydraulic circuit will not compress the tissue any further.

Moreover, because of the piston arrangement, the stapling function is effectively locked out until tissue compression is complete. With this arrangement, fluid introduced via the fluid port 50b (FIG. 11A) into the staple fluid channel 122 prior to completion of tissue compression will leak until the two o-rings 112 of the compression piston 106 are straddling the inlet 114. This design prevents premature staple firing.

At the fully compressed position, the arm spreaders 110 are nearly perpendicular to the longitudinal centerline of the stapler head. Once tissue is compressed between cartridge 78 and anvil 96, the tissue is ready for stapling.

Stapling is initiated by introducing hydraulic fluid through port 50b (FIG. 5). The staple piston advances, pushing cutting element 86 (FIGS. 7 and 10) towards the anvil 96. Because the staple pusher 76 is mounted to the cutter 86, this action carries the staple pusher 76 through the cartridge 78 where it simultaneously pushes all staples through the tissue. Staple piston travel is limited by internal stops, and is preset to yield optimal staple formation.

During compression, as the angle at the hinge 104 of arm assemblies 32 reaches its minimum, the force required to resist separation of the staple and anvil housings increases. These forces increase further when the forces of staple crushing are exerted on the anvil by the staple piston. To compensate, the arm spreaders 110 serve as displacement struts to channel at least a portion of these forces into the disk 68. These forces, if not reacted by the pusher disk, would pull in the arms 100, 102 and potentially release the compression on the tissue, causing incomplete staple formation or tissue cutting. In this way, a truss-like structure is created for force displacement.

When staples have been formed, staple pressure is released and a spring (not shown) returns the staple pusher 72 to its base position. Releasing fluid pressure will allow the deflected spring wires 46 on membrane raiser 37 to return the staple head to its minimum profile configuration and release the plication from the stapler. Once outside the patient, the used staple cartridge can be ejected and a new one installed.

Figure 25A:
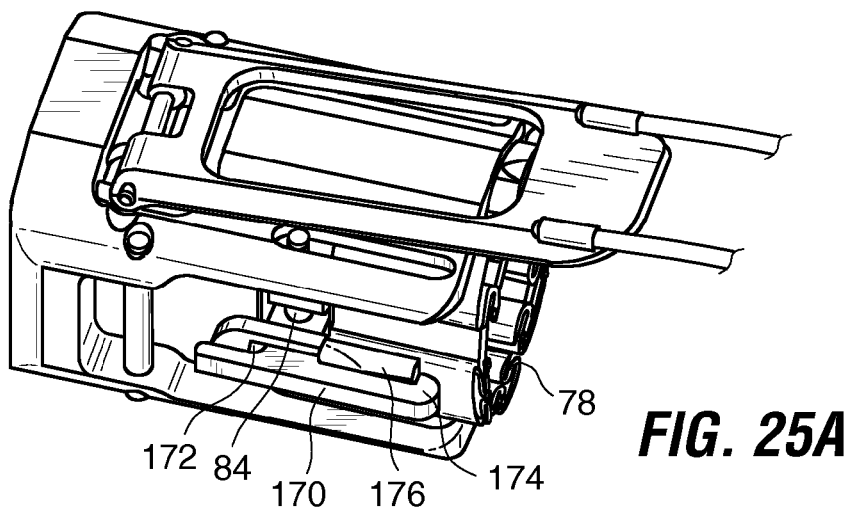
FIGS. 25A-25B are perspective views showing the staple housing, cartridge and a portion of the membrane raiser. These figures illustrate the steps of detaching a staple cartridge from the staple housing.
Figure 25B:
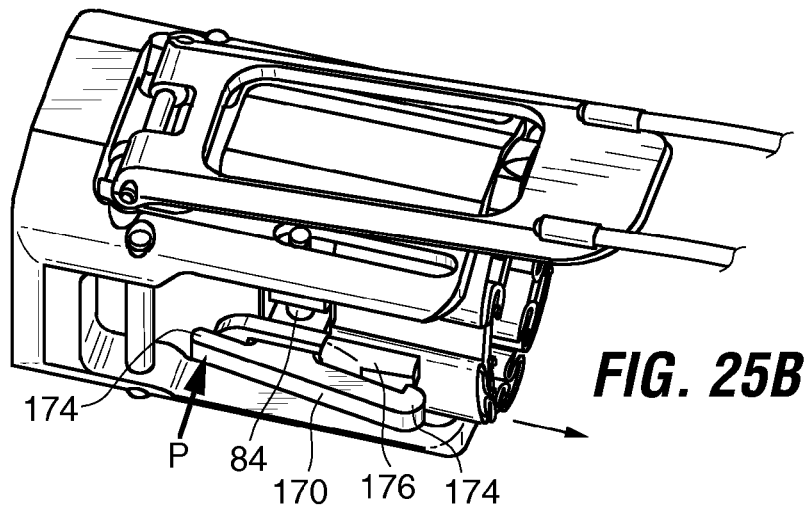
Figure 25C:
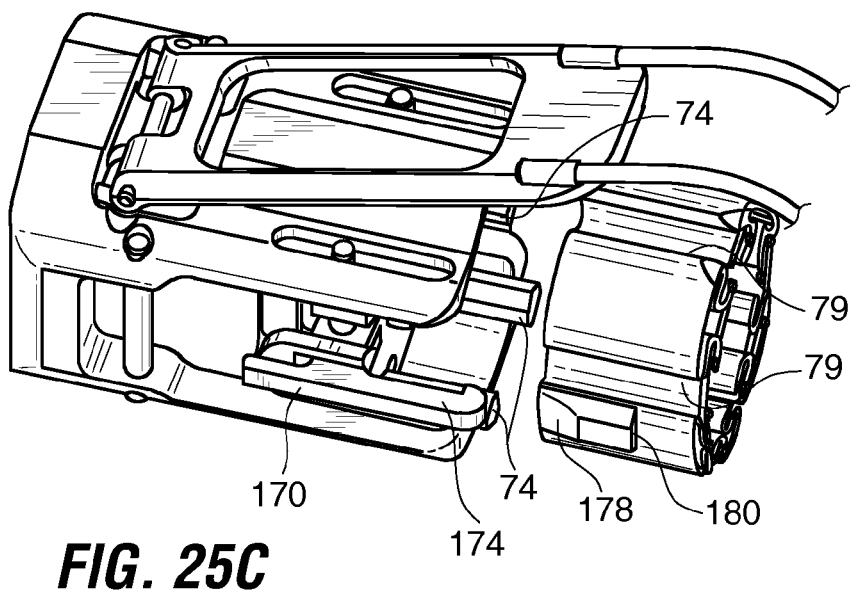

FIGS. 25A-25C illustrate one method for retaining a removable staple cartridge 78 within the staple housing. The cartridge is spring-loaded into the staple housing and retained by two latches 170 (one visible), each pivotable relative to a fulcrum 172. As shown, the fulcrum 172 may be coupled to the disk 68 by pin 84. Each latch 170 includes a catch 174 which engages a corresponding catch 176 on the cartridge. The latch 170 is preferably spring biased to urge the catch 174 inwardly towards the cartridge.

Depressing the proximal end 175 of each latch 170 as shown by arrow P in FIG. 25B pivots the latch against this bias, causing ejection of the staple cartridge. A new staple cartridge may then be positioned with its grooves 79 aligned with alignment posts 74 as shown in FIG. 25C and then pushed towards the staple housing. As the new cartridge slides into position, catch 174 rides over the tapered proximal portion 178 of the catch 176. Once catch 174 passes over the distal end 180 of the catch 176, it drops inwardly towards the cartridge due to its spring bias, thus engaging the cartridge. When the cartridge is properly seated, a click will be felt or heard as the latches engage the new cartridge.

Stapler Shaft and Handle

Referring again to FIG. 2, the stapler shaft 16 connecting the handle 18 and the stapler head 14 is flexible enough to conform to the curvature of the upper digestive tract, yet maintains the ability to transmit enough torque to rotate the stapler head. The shaft is formed with sufficient stiffness to allow it to be pushed down esophageal guide tube 23. Suitable materials include FIG. 26 shows a distal portion of the shaft 16, with the stapler head removed from the shaft. As shown, shaft 16 includes an endoscope lumen 124 through which an endoscope is advanced to allow visualization of a stapling operation. Side lumens 126 may also be provided for receiving other instruments useful during the procedure.

An articulating section 128 is positioned at the distal end of the shaft 16, between the shaft 16 and the stapler head 14 so as to allow the stapler head to be articulated relative to the shaft. Tubing coupled to the vacuum source and the source of hydraulic fluid extends from the handle and through the shaft 16 and the articulating section 128.

FIG. 27A shows one configuration that may be used for the hydraulic fluid lines 130. During use, the hydraulic fluid lines are subjected to significant deflection and elongation in the articulating section of the stapler. They are also subjected at times to fluid pressure which may be in excess of 1000 psi. Typically, hydraulic lines in industrial applications are flexible and have a working loop of extra tubing that accommodates length changes during use. The illustrated configuration for the hydraulic lines is a lower profile solution particularly suitable for an endoscopic device having space constraints. A preferred hydraulic line is a tube 130 having a portion that is shaped into a longitudinally expandable shape so that it can accommodate effective length changes during bending. The longitudinally expandable portion of the tube is preferably disposed within the articulating section 128 of the stapler 12. In a preferred design, the longitudinally expandable shape is a coil shape as shown in FIG. 27A. In alternate embodiments, the tube 130 may be formed into other longitudinally expandable shapes, such as regular or irregular undulating shapes (FIG. 27B).

The preferred material for the tubes 130 is stainless steel hypotube, although other materials may instead be used. In the preferred stapler configuration, two drive fluid lines are provided, one for actuating tissue compression, and the other for staple application (and cutting when used). In the present embodiment, the tubes are coiled together as shown in FIG. 27A. In alternate embodiments, two or more coiled tubes may be nested one inside the other. As the articulating section bends, it forces the coiled tubes 130 to bend and to change length in response to bending. The coiled tubes behave just as coiled wires would during these motions and are thus able to change length, deflect, and follow the contour of the articulating section without compromising flow through the lumens of the tubes or imparting undue stress to the connections at either end of the hydraulic system.

The longitudinally expandable shapes for the fluid lines may be suitable for use in allowing delivery of fluid to the operative ends of other types of articulating medical devices, such as catheters or endoscopic devices for delivering therapeutic agents or irrigation fluids past an articulating or bendable section of the device.

Figure 3C:
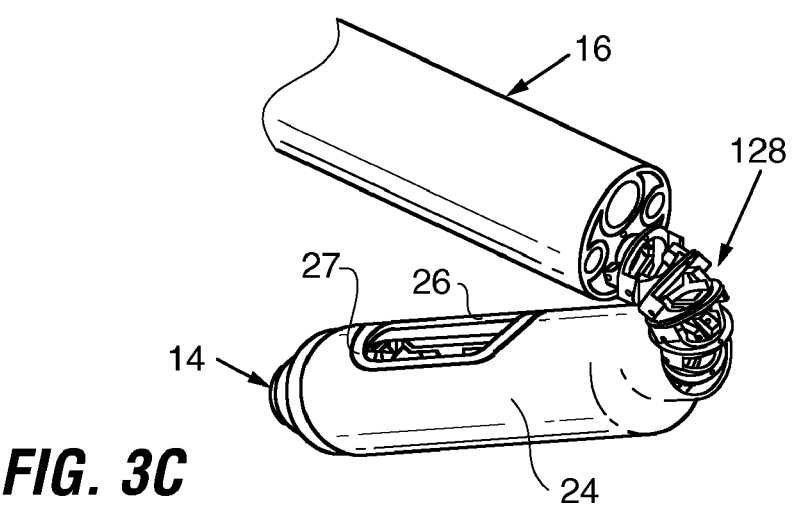

Referring again to FIG. 26, articulating section 128 is comprised of a spine formed of a plurality of links 132 strung over a pair of pull cables 134 (only one shown in FIG. 26). In one embodiment, engagement of the pull cables allows the stapler head 14 to be articulated in two directions through a range of motion of approximately 90 degrees in one direction (see FIG. 3B) to 175 degrees in the opposite direction (see FIG. 3C). Each pull cable is anchored at or near the stapler head, such as at the distalmost link 132 of the stapler housing 28.

The more proximal portions of the pull cables 134 extend the length of the shaft 16 and terminate in the handle 18. Referring to FIG. 28, the handle 18 includes a rotating knob 136 that may be selectively rotated in a clockwise or counterclockwise to articulate the stapler head up or down. Rotation in one direction applies tension to one of the pull cables to cause the stapler head to bend downwardly, whereas rotation in the opposite direction puts tension on the other cable, causing the head to bend upwardly.

In a preferred handle configuration, the knob 136 includes an internal threaded bore 138. Knob 136 is partially restrained within the handle 18 so that it remains fixed within the handle but can rotate freely. A carriage 140 having a threaded exterior surface is positioned within the threaded bore 128 of the knob. The threads within the bore 138 are engaged with the threads on the carriage 140 so that rotation of the knob causes the carriage 140 to translate, but not rotate, within the handle.

Each of the two pull cables, identified in FIG. 28 as cables 134a and 134b, is terminated on a different member in the handle. Cable 134a is mounted on the sliding carriage and cable 134b is mounted to a stationary part of the handle 18. Each cable extends through a corresponding sheath. Cable 134a extends through a sheath 135a having a proximal end fixed to a stationary part of the handle 18. Cable 134b extends through a sheath 135b having a proximal end mounted to the sliding carriage.

The cables 134a,b and sheaths 135a,b are arranged such that translation of the carriage in one direction will cause deflection of the stapler head in one direction, and translation of the carriage on the other direction will deflect the stapler head in another direction.

Referring to FIG. 28, if knob 136 is rotated to causes the carriage 140 to translate to the left of the page, cable 134a will be tensioned and cable 134b will slacken, causing the stapler head to articulate in a first direction (e.g. upwardly). Rotation of the knob 136 in the opposite direction will advance the carriage to the right of the page, releasing tension on cable 134a and pushing sheath 135b over the cable 134b towards the distal end of the staple head, causing articulation in the second direction (e.g. downwardly) as the sheath 135b is advanced against a distal portion of the shaft 16. The proximal portion of sheath 135b is provided with sufficient working length prevent it from being placed under tension when the carriage moves distally. The positioning of the knob is advantageous in that the hand movement required for stapler articulation is always the same, regardless of the rotational orientation of the stapler. Also, the use of the threaded knob can prevent unintentional relaxation of the deflection angle, even if the knob is provided without a lock to retain its rotational position.

Figure 29:
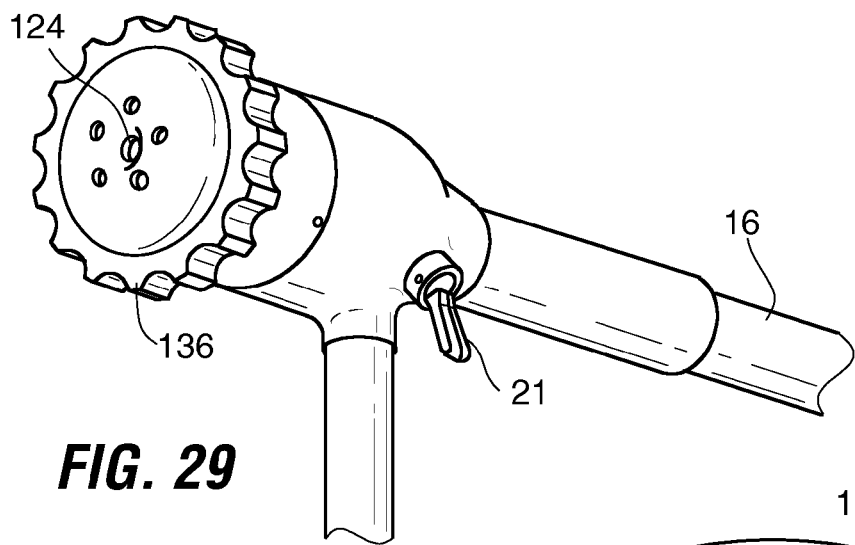
FIG. 29 is a perspective view of the handle of the stapler of FIG. 2.

Referring to FIGS. 28 and 29, the endoscope lumen 124 extends along the center axis of the stapler. The positioning of the lumen and the coaxial relationship of the articulation knob in relative to the endoscope 124 allows the endoscope and stapler to be rotated independently without one interfering with one another. Thus, if the user chooses to change the rotational orientation of the stapler head 14 within the body, s/he may rotate the handle 18 and shaft 16 while maintaining the rotational position of the endoscope.

For cost efficiency, the stapler 12 may be designed to permit the stapler head 14 to be discarded while allowing the shaft 16 and handle 18 to be sterilized and re-used. One mechanism for removably coupling the stapler head to the shaft 16 is illustrated, although others are readily conceivable (e.g. a slip coupling type arrangement). Referring to FIG. 26, an end plate 142 is mounted to the distalmost one of the links 132. Each of the end plate 142 and the corresponding rear surface of the stapler head are provided with latch features that allow the end plate and stapler head to be engaged to one another.

End plate 142 includes a cantilevered pin 144 having a peg 145 (which may be a spring pin), a central opening 146, and a pair of u-shaped catches 148 along its edges. Hydraulic feed holes 156a, b are formed through the end plate 142. The hydraulic tubes that deliver hydraulic fluid to the stapler head (see tubes 130 of FIG. 27) are preferably welded to the end plate to allow fluid from the tubes to be directed through the feed holes 156a, b.

Figure 30A:
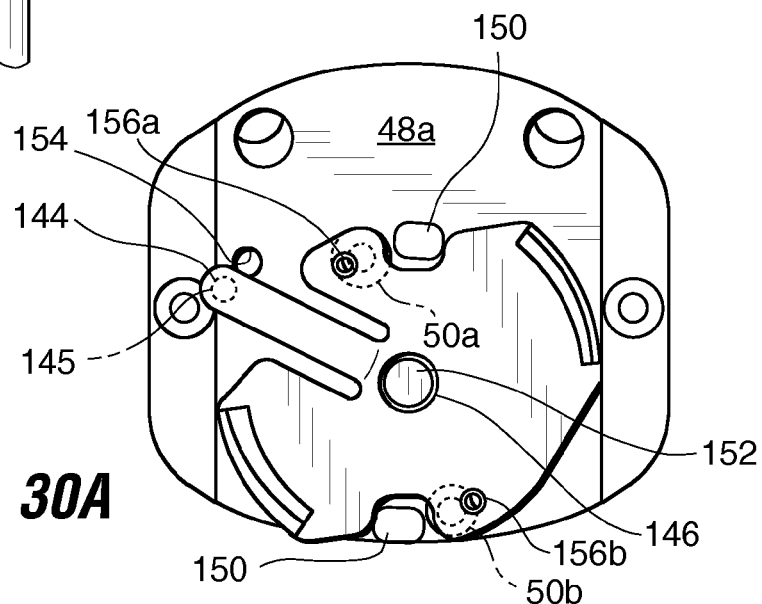
FIGS. 30A and 30B are plan views of the proximal face of the staple housing, showing a method for attaching the end plate of the stapler handle to the staple housing.
Figure 30B:
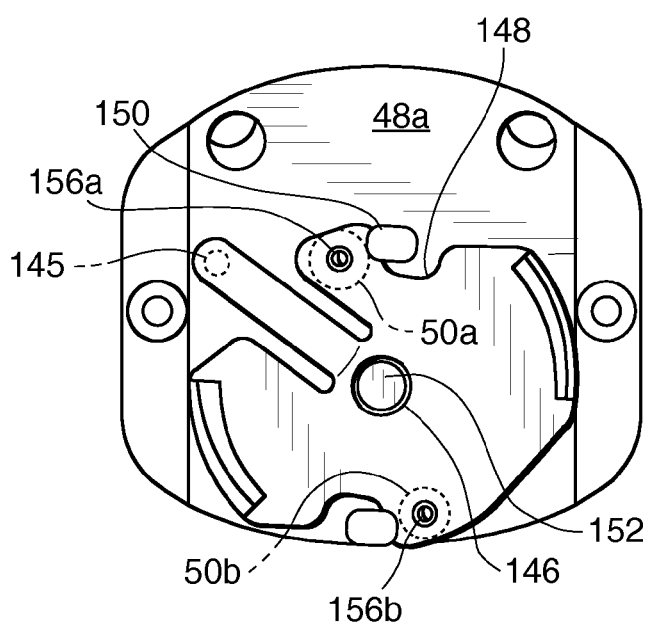

FIGS. 30A and 30B show the rear surface 48a of the staple housing, which has been somewhat modified relative to FIG. 5. In this variation of the rear surface 48a, the hydraulic input ports 50a, 50b are repositioned as shown. Additionally, the rear surface 48a has been modified to include a pair of catches in the form of undercut bosses 150, plus an aligning pin 152, and a hole 154.

FIGS. 30A and 30B show the end plate 142 positioned against the rear surface 48a of the staple housing. The other features of the articulating section 128 are not shown in FIGS. 30A and 30B for clarity. To attach the stapler head to the shaft 16, the plate 142, attached to the handle assembly, is pressed against the rear surface 48a of the staple housing as shown in FIG. 30A. As the plate is pushed, it is rotated in a clockwise direction, causing the peg 145 (FIG. 26) of the cantilevered pin 144 to engage hole 154 in the rear surface of the staple housing. When this latch is engaged, hydraulic feed holes 156a, b of the end plate 142 are lined up with the hydraulic inlets 50a, 50b on the staple head as shown in FIG. 30B. At the same time, portions of the end plate surrounding u-shaped catches 148 slide beneath the undercut bosses 152. Pressing the plate compresses the face-sealing o-rings surrounding the hydraulic input ports 50a, 50b. Compression on the o-rings is maintained by engagement of the catches and the undercut bosses overhanging the end plate. To remove the stapler head from the housing, the stapler housing is twisted in a counter-clockwise direction to disengage the end plate 142 from the rear surface 48a. The stapler shaft and handle may then be sterilized in preparation for mounting of a fresh stapler head.

Exemplary Procedure

One example of a method for using the system 10 will next be described in the context of formation of plications in stomach wall tissue.

As an initial step (FIG. 2), endoscopic guide tube 23 is advanced into the stomach via the mouth and esophagus. The endoscope 22 is inserted into the endoscope channel in the stapler handle (not shown) and advanced down the lumen of the stapler handle. The stapler/endoscope are simultaneously passed through the endoscopic guide tube towards the stomach. Once the stapler and endoscope reach the gastroesophageal junction region of the stomach, the position of the stapler is maintained while the endoscope is advance further into the stomach.

Figure 31A:
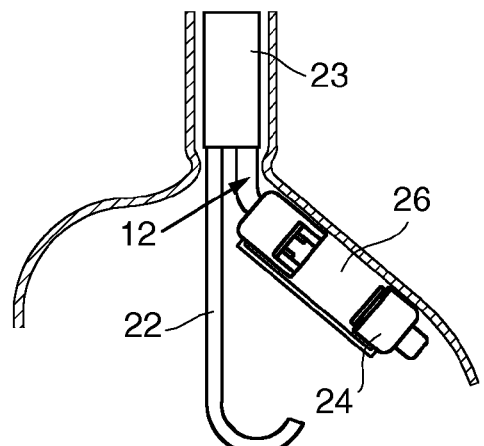
FIGS. 31A-31E are a series of drawings schematically illustrating use of the system of FIG. 2 to form a plication in a stomach.

The stapler head 14 is advanced to the desired depth and location in the stomach. Using the articulation controls on the stapler handle, the angular orientation of the stapler head is adjusted to allow positioning of the stapler head 12 at the pre-identified target tissue as shown in FIG. 31A. The opening 26 in the membrane 24 is positioned against the target tissue. The endoscope 22 is placed in a retroflexed position as shown.

Figure 31B:
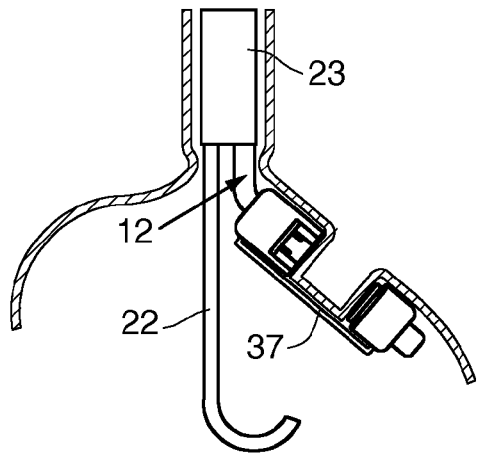
Figure 32C:
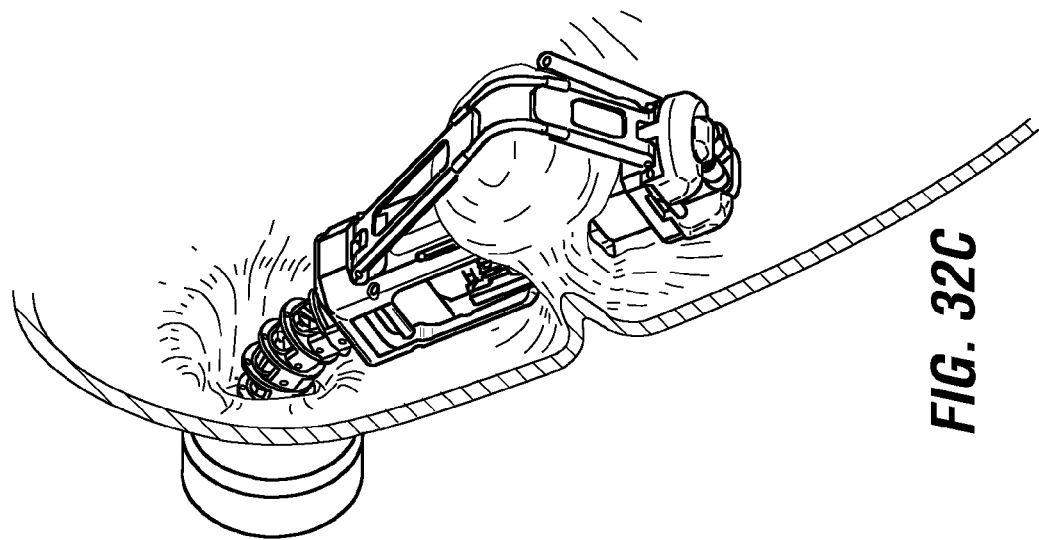
FIGS. 32A-32C are a series of perspective views illustrating use of the stapler of FIG. 2 to acquire, compress, and then staple stomach wall tissue to form a plication in the stomach. The membrane is not shown in these drawings.
Figure 32B:
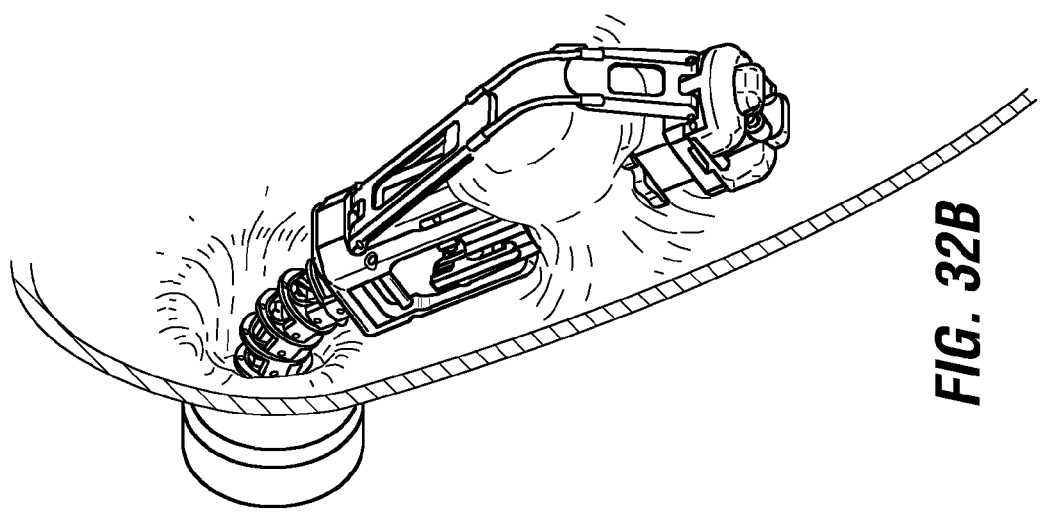
Figure 32A:
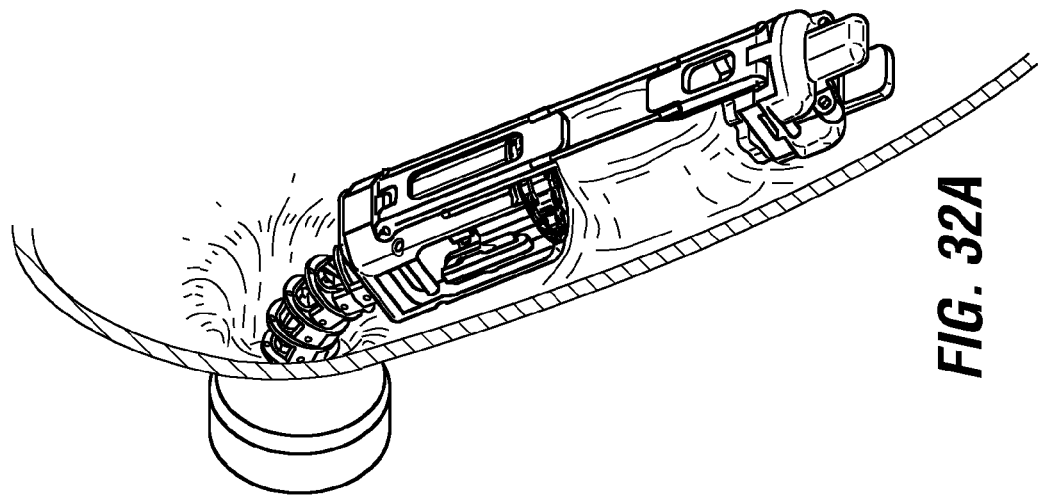

The vacuum source 20 (FIG. 2) is coupled to the vacuum port on the handle external to the body, and vacuum pressure is applied to draw tissue through the opening 26 and into the vacuum chamber defined by membrane 24 as shown in FIGS. 31B and 32A. Acquisition of the target tissue will be readily identified endscopically through the wall of transparent membrane 24 on the stapler head.

Figure 31C:
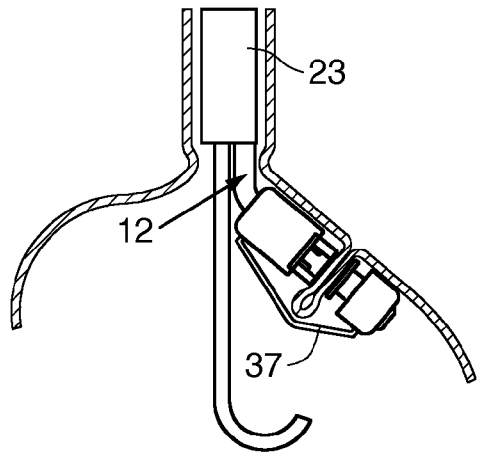

The fluid source (is shown) is coupled to the handle. Once it has been visually confirmed that a sufficient amount of tissue has been acquired, fluid is introduced to cause compression of the tissue and expansion of the arm assemblies 32 and membrane raiser 37 as shown in FIGS. 32B and 31C. As can been seen, the expansion of the arm assemblies and the membrane allows a large volume of tissue to be acquired into the vacuum chamber and displaced further into the chamber during tissue compression.

Figure 31D:
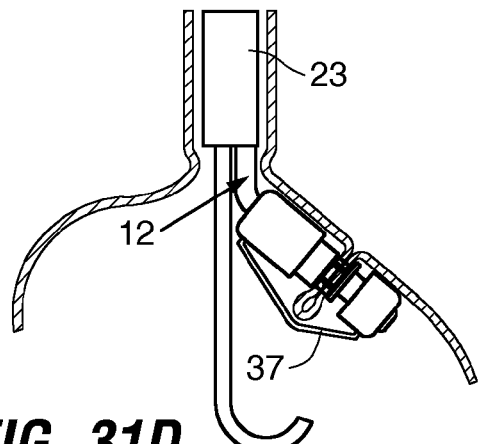
Figure 31E:
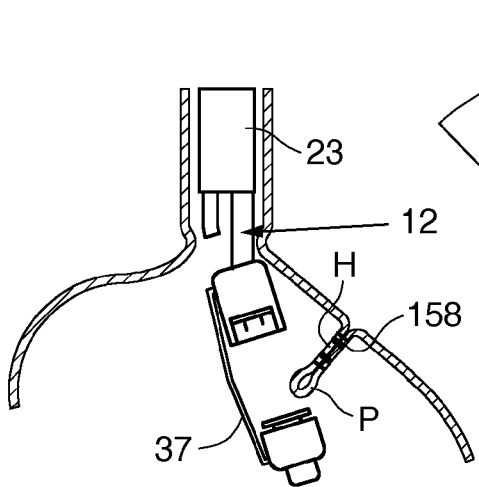

Once the tissue has been compressed, additional hydraulic fluid is introduced to cause stapling and cutting of the tissue as shown in FIGS. 31D and 32C, forming a plication P. The compression and stapling hydraulic sources are then deactivated to release fluid pressure within the hydraulic circuit. With the hydraulic pressure relieved, the spring wires of the membrane raiser 37 help to restore the stapler head 14 to its original streamlined configuration, allowing the stapler head to be withdrawn from the tissue as shown in FIG. 31E. The stapler head may be articulated relative to the shaft to assist in moving the stapler head away from the plication P.

Figure 33:
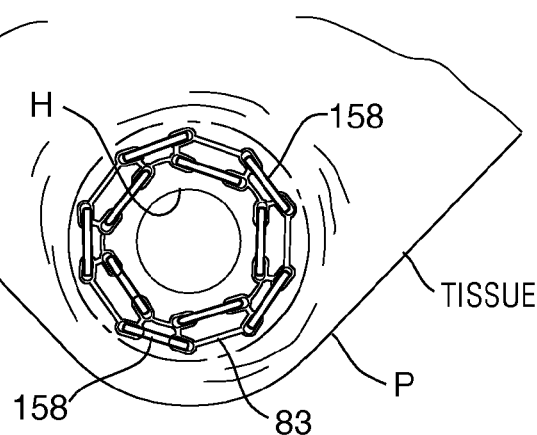
FIG. 33 is a top plan view of a plication formed in body tissue.

In a preferred plication configuration shown in FIG. 33 the staples 158 are arranged in two concentric rings of five staples, with the staple reinforcement device 83 retained by the staples and distributing forces around the staple pattern as shown. The plication P includes a hole H formed by the cutting element, through which various implants or anchors for various implants can be placed.

If multiple plications are needed, the stapler 12 is briefly withdrawn from the endoscopic guide tube and the staple cartridge is replaced in the manner described in connection with FIGS. 25A-25C. The procedure is repeated until all desired plications have been formed.

The system may be packaged with instructions for use instructing the user to use the various disclosed features to perform a stapling procedure using methods disclosed herein.

Alternate Embodiments

Figure 34:
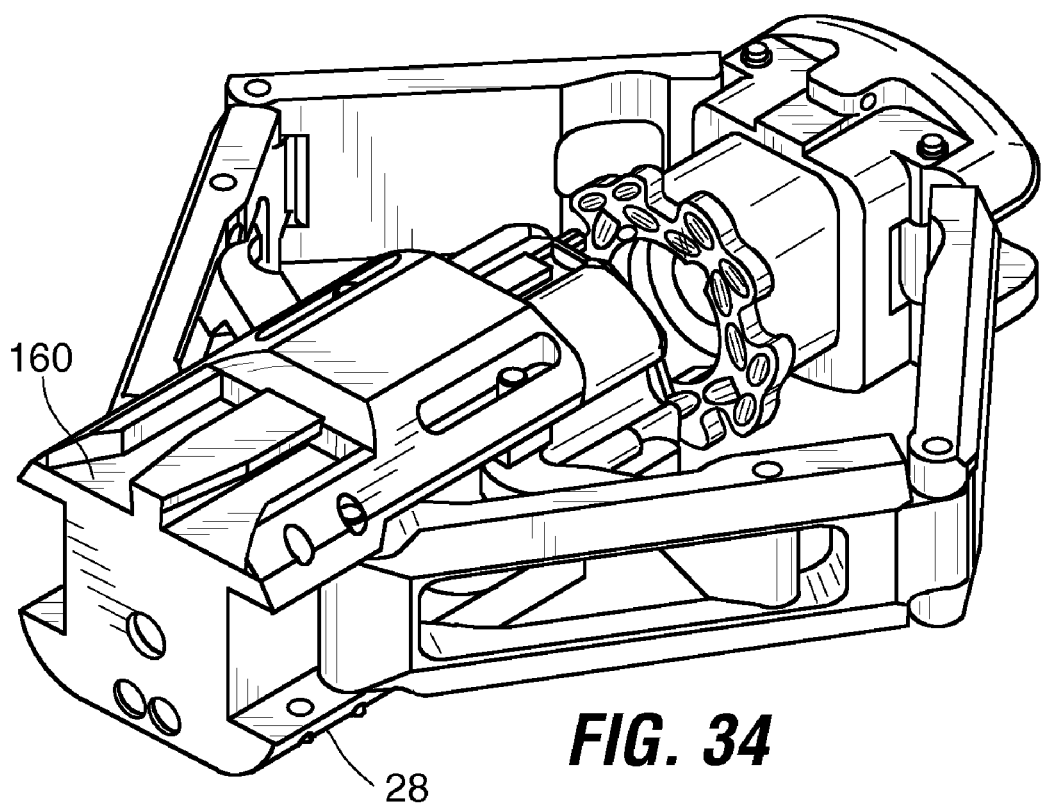
FIGS. 34 and 35 are perspective views of an alternative stapler head equipped to carry additional tools.
Figure 35:
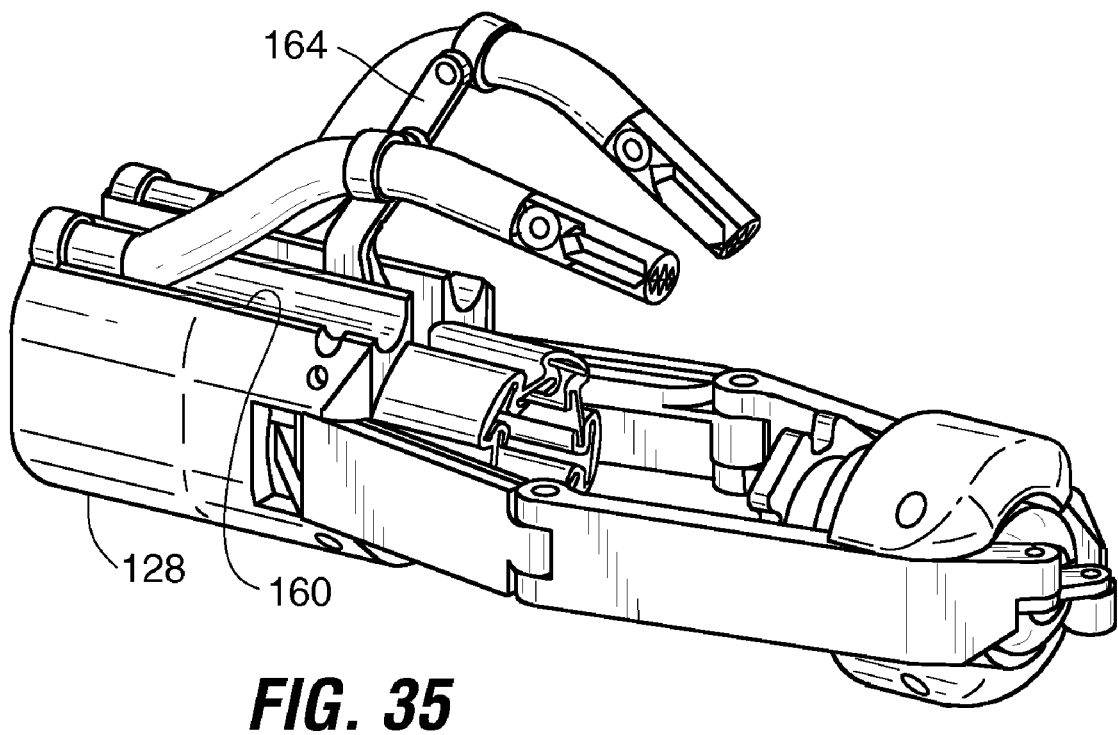

The basic architecture of the stapler disclosed above can be used as a foundation for other stapling tools. FIGS. 34-35 show a modified stapler in which the membrane and membrane raiser have been removed, and in which the staple housing 28 has been modified for the attachment of tools. As shown in FIG. 34, the staple housing 28 includes a pair of grooves 160 proportioned to receive tools 162. Tools 162 may be seated in these grooves 160 and mounted to the staple housing as shown in FIG. 35. This attachment will provide for a stable base from which to actuate the tools. The tools may be self-articulating, or the staple housing 28 may be equipped with devices 164 for moving the tools between streamlined positions for insertion of the assembly into a body cavity, and a deployed position such as that shown in FIG. 35. Tools similar to those in FIG. 35 might be used for tissue acquisition, by reaching between the cartridge and anvil and used to engage tissue and pull the tissue into position between the cartridge and anvil so that it may be stapled, or otherwise affected by various features added to or in place of the anvil and cartridge. Procedures which may benefit from adaptation of the stapler include, but are not limited to gastroplasty, stoma adjustment, polyectomy, lead placement, bleeding control, perforation or hole closure, biopsy and tumor removal.

The disclosed systems provide convenient embodiments for carrying out the disclosed compression and stapling functions. However, there are many other widely varying instruments or systems may alternatively be used within the scope of the present invention. Moreover, features of the disclosed embodiments may be combined with one another and with other features in varying ways to produce additional embodiments. Thus, the embodiments described herein should be treated as representative examples of systems useful for forming endoscopic tissue plications, and should not be used to limit the scope of the claimed invention.

Any and all patents, patent applications and printed publications referred to above, including those relied upon for purposes of priority, are incorporated herein by reference.

We claim:

1. A medical instrument for carrying out a remote surgical operation within an internal organ, comprising:
   a shaft having a distal end and a proximal end;
   a surgical device that is operated by a compressed fluid;
   an articulated spine section connecting the distal end of the shaft to a proximal end of the surgical device, said spine comprising a plurality of links positioned between the shaft and the surgical device;
   at least one cable extending through the shaft and openings in the links in the articulated spine, by which the position of the device relative to the shaft can be controlled at the proximal end of the shaft; and a compressed-fluid tube extending through the shaft and through the openings in the links of the articulated spine, through which a compressed fluid can be supplied to the device from the proximal end of the shaft.

2. The medical instrument according to claim 1, further including:

a fluid port in the surgical device, wherein the fluid tube and fluid port are fluidly coupled to one another when the device is coupled to the shaft.

3. The medical instrument of claim 2, wherein:

the surgical device is a stapler head having a fastener housing and an anvil housing, the fastener housing having
  a hydraulic chamber disposed within the fastener housing,
  a compression piston at least partially disposed within the hydraulic chamber for movement therein,
  a second chamber disposed within the compression piston,
  a staple piston at least partially disposed within the second chamber for movement therein,
  a staple holder carrying at least one fastener, the staple holder being attached to the compression piston for movement therewith in the fastener housing; and
  a staple driver coupled to the staple piston such that directing fluid from the fluid line into the second chamber advances the staple driver at least partially through the staple holder.

4. The medical instrument of claim 1, wherein the articulated spine section includes an end plate at its distalmost end, the end plate having an opening;

the surgical device includes an alignment pin, the alignment pin insertable into the opening in the end plate; and wherein the end plate and surgical device are rotatable relative to the alignment pin to a latched position in which the end plate and surgical device engage with one another.

5. The medical instrument of claim 4, wherein the surgical device includes a boss having an undercut on a proximal end that faces the end plate, and the end plate includes a member rotatable into an engaged positioned beneath the undercut.

6. The medical instrument of claim 4, wherein the surgical device includes a second pin on a proximal end that faces the end plate and the end plate includes pin opening positioned such that relative rotation of the end plate and the surgical device causes the second pin to engage with the pin opening.

7. The medical instrument of claim 4, wherein the end plate includes a first drive fluid feed hole and the surgical device includes a first drive fluid inlet, and wherein the feed hole and inlet are positioned such that rotation of the end plate and surgical device to the latched position moves the first feed hole and inlet in alignment with one another.

8. The medical instrument of claim 7, wherein the compressed-fluid tube extends through the shaft, through the openings in the links of the articulated spine section, through the feed hole in the end plate, and into the inlet in the proximal end of the surgical device.

9. The medical instrument of claim 1, wherein the surgical device has a proximal face that faces the articulated spine section, the instrument further comprising:

an end plate at a distalmost end of the articulated spine section, the end plate having a first face that faces toward a second face of the surgical device; and a latch having a first feature on the first face and a second feature on the second face, the first and second features being engageable with one another to removably couple the surgical device to the articulated spine section.

10. The medical instrument of claim 1, further comprising:
a handle positioned at the proximal end of the shaft;
a knob rotatably mounted on the handle;
wherein the at least one cable comprises a first cable and a second cable;
the first cable extending from the handle, through the shaft and the articulated spine section, the first cable being anchored to the knob and a distal end of the articulated spine section;
the second cable extending from the handle, through the shaft and being anchored to the knob and the distal end of the articulated spine section;
wherein the knob is rotatable from a first position to a second position to apply tension to the first cable and thereby cause deflection of the articulated spine section in a first direction; and
wherein the knob is rotatable from the second position to the first position to apply tension to the second cable and thereby cause deflection of the articulated spine section in a second direction.

11. The medical instrument of claim 10, wherein rotating the knob in the first direction articulates the surgical device through a range of motion up to 90° in the first direction and through a range of motion up to 175° in the second direction.

12. The medical instrument of claim 10, wherein the distal end of the articulated spine section includes an end plate; and the first and second cables are anchored to the end plate.

13. The medical instrument of claim 1, wherein the surgical device is a fastener head comprising:

a fastener member having a fastener housing and a staple holder that is independently moveable with respect to the fastener housing; and an anvil member having an anvil housing and an anvil that is independently movable with respect to the anvil housing carried on the anvil housing;

the housings defining a region therebetween where tissue can be received.

14. The medical instrument of claim 13, further comprising:

an arm assembly operatively coupled to the fastener member and the anvil member; and a drive assembly including a drive member operatively coupled to the staple holder for movement within the fastener housing from a retracted position to an extended position such that movement of the drive member from its retracted to its extended position is effective to (i) move the staple holder with respect to the fastener housing toward the anvil, (ii) move the anvil member toward the staple member, and (iii) move the anvil with respect to the anvil housing toward the staple holder.

15. The medical instrument of claim 14, wherein the anvil member includes drive links operatively connected to the arm assembly for moving the anvil toward the staple holder as the drive assembly is moved from its retracted to its extended position.

16. The medical instrument of claim 13, wherein the drive member includes a disc that travels within the fastener housing, and carries at least one pin that moves within a slot in the fastener housing, thereby limiting the extent of travel of the drive member toward its extended position to the extent of travel allowed for the pin within the slot; and wherein the slot is proportioned such that the pin abuts an end of the slot when the fastener and anvil members reach the second relative position to prevent further movement of the drive member.

17. The medical instrument of claim 16, further comprising:
at least one arm spreader pivotally connecting the disc to the arm assembly for spreading the arm assembly outwardly as the disc travels from its retracted to its extended position.

18. The medical instrument of claim 16, wherein the drive member includes a drive piston connected to the disc, and which further includes a staple piston carried for movement within the drive piston between retracted and extended positions; and
a staple pusher adapted to engage one or more staples in the staple holder and eject the one or more staples from the holder against the anvil when the staple pusher is moved with the staple piston from a retracted to an extended position.

19. The medical instrument of claim 16, wherein the disc has at least one axially extending post adapted to engage the staple and prevent angular movement of the cartridge within the staple housing.

20. The medical instrument of claim 13, wherein the staple holder is designed to hold an annular array of staples, and
wherein the staple pusher is adapted to engage and eject the array of staples simultaneously.

21. The medical instrument of claim 13, wherein the staple holder is a replaceable staple cartridge adapted to be inserted into the staple housing to travel therein with the drive member between retracted and extended positions.

22. The medical instrument of claim 21, further comprising:
a cartridge-side reinforcing ring disposed against the cartridge and having openings for receiving staples therethrough for attaching the reinforcing ring to the side of stapled tissue facing the cartridge.

23. The medical instrument of claim 13, further comprising:
a tissue cutter mounted on the staple driver, the cutter being adapted to cut a hole in a tissue fold held between the staple holder and anvil as a tissue fold is being stapled by movement of the staple piston from its retracted to its extended position.

24. The medical instrument of claim 23, wherein the anvil member includes a compressible cutting board which allows the cutter to be advanced by movement of the staple driver beyond the cutter's point of initial contact with the cutting board.

25. The medical instrument of claim 24, wherein the cutting board is formed of a material that can be penetrated by the cutter.

26. The medical instrument e of claim 24, wherein the cutting board is formed of silicone.

27. The medical instrument of claim 24, wherein the cutting board is spring biased in the direction opposing movement of the cutter.

28. The medical instrument of claim 13, further comprising:
an alignment pin carried on one of the fastener or anvil members; and
an opening on the other of the fastener or anvil members, said pin and opening being positioned such that movement of the drive member toward its extended position causes the pin to mate with the opening, thus to engage the two members.

* * * * *

UNITED STATES PATENT AND TRADEMARK OFFICE
CERTIFICATE OF CORRECTION

Page 1 of 1

PATENT NO.      : 7,913,892 B2
APPLICATION NO. : 12/053182
DATED           : March 29, 2011
INVENTOR(S)     : David Cole and Andrew Smith It is certified that error appears in the above-identified patent and that said Letters Patent is hereby corrected as shown below:

IN THE CLAIMS:

Claim 6, column 17, line 47, "end plate and the end plate includes pin opening positioned" should be changed to --end plate and the end plate includes a pin opening positioned--.

Signed and Sealed this
Sixteenth Day of August, 2011

David J. Kappos
*Director of the United States Patent and Trademark Office*